United States Patent [19]

Arima et al.

[11] Patent Number: 5,275,947
[45] Date of Patent: Jan. 4, 1994

[54] NON-A, NON-B HEPATITIS VIRUS ANTIGEN PEPTIDE

[75] Inventors: Terukatsu Arima, Okayama; Konosuke Fukai, Toyonaka, both of Japan

[73] Assignee: The Research Foundation for Microbial Disease of Osaka University, Osaka, Japan

[21] Appl. No.: 24,973

[22] Filed: Mar. 2, 1993

Related U.S. Application Data

[62] Division of Ser. No. 401,271, Aug. 31, 1989, Pat. No. 5,191,064.

[30] Foreign Application Priority Data

Mar. 4, 1989 [JP] Japan .................................. 1-52642
Jun. 14, 1989 [JP] Japan ................................ 1-153257
Jul. 25, 1989 [JP] Japan ................................ 1-193233

[51] Int. Cl.$^5$ .................... C12N 1/20; C07H 19/00; C07H 17/00
[52] U.S. Cl. ..................... 435/252.33; 435/252.3; 536/22.1; 536/23.1; 536/23.5
[58] Field of Search .............. 435/7.1, 69.1, 69.3, 435/252.3, 252.33, 320.1; 536/22.1, 23.1, 23.5

[56] References Cited

FOREIGN PATENT DOCUMENTS 0318216 5/1989 European Pat. Off. .

*Primary Examiner*—Robert A. Wax
*Assistant Examiner*—Hyosuk Kim
*Attorney, Agent, or Firm*—Armstrong, Westerman, Hattori, McLeland & Naughton

[57] ABSTRACT

Disclosed is a non-A, non-B hepatitis virus antigen peptide which exhibits antigen-antibody reaction specificity with at least one of sera from a convalescent patient having acute non-A, non-B hepatitis and sera from a patient having chronic non-A, non-B hepatitis. By the use of the antigen peptide of the present invention, not only the diagnosis of non-A, non-B hepatitis but also the screening of blood for transfusion can be achieved with ease and high reliability. The antigen peptide of the present invention may also be used as the basis for a vaccine against non-A, non-B hepatitis.

4 Claims, 7 Drawing Sheets

FIG. 2(a)

```
         10        20        30        40        50        60
GAATTCCAAAAGAGCAAAACAAACCGGCCGAAGAAAAACTAATAAGAGAAGAAAAAGGCG
CTTAAGGTTTTCTCGTTTTGTTTGGCGGCTTCTTTTTGATTATTCTCTCTTTTCCGC 70        80        90        100       110       120
AAGAGACACAGGAAAAAAAACAGAGACGAAGGTCAGATAGAAAAAAAGCAAGGAATTC
TTCTCTGTGTCCTTTTTTTTTGTCTCTGCTTCCAGTCTATCTTTTTTTCGTTCCTTAAG
```

FIG. 2 (b)

```
         10        20        30        40        50        60
GAATTCCGAGAACAAGACCAGATAAAACCAAAGACAACAAGAGAAAGACGAAA
CTTAAGGCTCTTGTTCTGGTCTATTTTGGTTTCTGTTCTTGTGTTCTCTTTCTGCTTT 70        80        90       100       110       120
AGAAGCACCAATCGCAGGCGAAGCAAAACGAAAAAAAAAAAAAAAGGAATTC
TCTTCGTGGTTAGCGTCCGCTTCGTTTTGCTTTTTTTTTTTTTTCCTTAAG
```

FIG. 2(c)

```
         10        20        30        40        50        60
GAATTCCAAGAAAAAAAGGGAGAAGCCAGCAATGGAGAAGCCGAAAACGACACACACAAG
CTTAAGGTTCTTTTTTTCCCTCTTCGGTCGTTACCCTCTTCGGCTTTGCTGTGTGTTC 70        80        90       100       110       120
AAACAAAGGAGGTACAAAGAAAAAGAAGAAAAACGGCAACAAATAACCCAGGAAAAGAACAAA
TTGTTTCCTCCATGTTTCTTTTTCTTTTTTTGCCGTTGTTTATTGGGTCCTTTTCTTGTTT 130       140       150       160       170       180
AAGCCAAGAGTGGGCAGAATAAAAAAACTGGAACCGGGGAAGGAAGGAAGGACGCATATCAG
TTCGGTTCTCACCCGTCTTATTTTTTGACCTTGGCCCCTTCCTTCCTTCCTGCGTATAGTC 190       200       210
ATTAGAAAAGGAGGGAATTC
TAATCTTTTCCTCCCTTAAG
```

FIG. 2 (d)

```
          10        20        30        40        50        60
GAATTCCTAAGAAATGGCTAGCCCTAGGAGAGGCAGTCTTTCCCCAGTCAGTTAGCCCGC
CTTAAGGATTCTTTACCGATCGGGATCCTCTCCGTCAGAAAGGGGTCAGTCAATCGGGCG 70        80        90       100       110       120
AAATGCCAGAGCATCAAGAATTCAGAAAAAGGAGAAAATATAGTTAATATCAAAGTGGTCG
TTTACGGTCTCGTAGTTCTTAAGTCTTTTTCCTCTTTTATATCAATTATAGTTTCACCAGC 130       140       150       160       170       180
AAGCCTAAGATAGAGAGGTAGAGAGTATGAAGAGTAAGACGAATACAAACCAAATTCTG
TTCGGATTCTATCTCTCCATCTCTCATACTTCTCATTCTGCTTATGTTTGGTTTAAGAC 190       200       210       220       230       240
GAATGATCATTAAAAACATTATTGATAGGTACTTAGAAGGGCAAGAGAGGAAGAAGAAAG
CTTACTAGTAATTTTTGTAATAACTATCCATGAATCTTCCCGTTCCTCTCCTTCTTCTTTC 250       260       270       280       290       300
TAATGAGAAATGCTTATGGAAGCCAAAGGAGCTTTCCAGGAGAAGAAAGGGAATTC
ATTACTCTTTACGAATACCTTCGGTTTCCTCGAAAGGTCCTCTTCTTTCCCTTAAG
```

FIG. 2 (e)

```
         10        20        30        40        50        60
GAATTCCCAACGGCGTCGGCTTGGCCCGGCCTTGGCCGCGACCCGCGCTGATGGCCGTG
CTTAAGGGTTGCGCAGCCGAACCGGGCGGAACCGGGCTGGGCGACTACCGGCAC

70
GAATTC
CTTAAG
```

FIG. 2(f)

```
          10        20        30        40        50        60
GAATTCCGGGGTATTTGCCTCGATTCTGCCTGCTCAGCGCTTCGGCCCTCGGCTTGGGCGC
CTTAAGGCCCCATAAACGGAGCTAAGACGGACGAGTCGCGAAGCCGGGAGCCGAACCCGCG 70        80        90       100       110       120
CCTGCTGCTGGCTTCCGAGCAGCTATTCAGCGCCCTTGAAAGTGGTTGGCGGGCGTACGT
GGACGACGACCGAAGGCTCGTCGATAAGTCGCGGAACTTTCACCAACCGCCGCCGCATGCA 130       140
GTCCGGGAATTC
CAGGCCCTTAAG
```

NON-A, NON-B HEPATITIS VIRUS ANTIGEN PEPTIDE

This is a division of application Ser. No. 401,271 filed Aug. 31, 1989, now U.S. Pat. No. 5,191,064.

BACKGROUND OF THE INVENTION

1. Field of the Invention

This invention relates to a non-A, non-B hepatitis virus antigen peptide. More particularly, the present invention is concerned with a non-A, non-B hepatitis virus antigen peptide which exhibits antigen-antibody reaction specificity with at least one of a convalescent serum from a patient having acute non-A, non-B hepatitis and a serum from a patient having chronic non-A, non-B hepatitis. The antigen peptide of the present invention is useful for diagnosing non-A, non-B hepatitis and for screening blood for transfusion. Further, the antigen peptide of the present invention can be used as an active ingredient of a vaccine for non-A, non-B hepatitis.

2. Discussion of Related Art

Definition of non-A, non-B hepatitis virus

The viral hepatitis is a liver disease caused by the infection of a hepatitis virus. Heretofore, hepatitis A virus, hepatitis B virus and hepatitis D (delta) virus have been isolated and identified. The hepatitis D virus (delta-hepatitis virus) is a deficient virus which cannot grow by itself and requires for its growth the co-presence of hepatitis B virus as a helper virus. Therefore, the hepatitis D virus is present only in a patient having hepatitis B. In 1974, it was reported that there were many patients having hepatitis caused by a factor other than the infection with either hepatitis A virus or hepatitis B virus. Such a hepatitis was named "non-A, non-B hepatitis", and researches on the non-A, non-B hepatitis virus have been made extensively and intensively throughout the world. Heretofore, it has been found that a plurality of types of non-A, non-B hepatitis viruses exist. Results of the researches up to now show that the non-A, non-B hepatitis virus is classified into two types according to the infection route, that is, an epidemic hepatitis virus, namely an enterically-transmitted non-A, non-B hepatitis virus, which is spread through water and foods; and a blood-transmitted non-A, non-B hepatitis virus which is spread through blood by transfusion, etc. Of the non-A, non-B hepatitis viruses, only an enterically-transmitted NANBV which spreads over the areas of Africa, India and Southeast Asia has been virologically identified, but the blood-transmitted non-A, non-B hepatitis virus has not yet been identified.

Hereinbelow, the blood-transmitted non-A, non-B hepatitis is often referred to simply as "NANB hepatitis", and the blood-transmitted non-A, non-B hepatitis virus is often referred to simply as "NANBV". Current situation of the studies on NANB hepatitis and Problems:

With respect to the mechanism of the crisis of the NANB hepatitis and the treatment of the NANB hepatitis, virological studies have been made in the world by the composition of NANBV with the other hepatitis viruses, diagnostic, histopathology and the like (Japan Medical Journal, No. 3220, pp. 3-10, 1987). With respect to the NANB hepatitis, the following findings have been reported.

(1) Epidemiology: In Japan, according to the estimation by Ministry of Health and Welfare, about 60% of chronic hepatitis patients (namely about 720 thousand patients), about 40% of hepatocirrhosis patients (namely about 100 thousand patients) and about 40% of liver cancer patients (namely about 7 thousand patients) are patients having NANB hepatitis. Further, the motality rate attributed to the above-mentioned NANB hepatitis reaches 16 thousand per year. In U.S.A., the number of post-transfusion hepatitis patients reaches 150 to 300 thousand per year and 90% of the post-transfusion hepatitis patients are patients having NANB hepatitis. Further, it is considered that 1 to 6% of the blood donors are an NANBV carrier. Further, it is estimated that in the other countries also, the incidence of NANB hepatitis and the ratio of the NANBV carrier are equal to or higher than those in U.S.A. and Japan. Therefore, prevention, early diagnosis and early treatment of the NANB hepatitis is a matter of global importance.

(2) Virology: The NANBV heretofore reported comprises an envelope and a viral particle having a spherical shape of a diameter of about 50 nm. The taxonomic observation suggests that the known NANBV is a virus similar to a togavirus or a flavivirus, or a virus of new type different from the togavirus or the flavivirus. Further, the results of pathological observations of the cytoplasms of hepatocytes of a plurality of chimpanzees injected with a blood serum of a patient having NANBV hepatitis show that the formation of a tubular structure is observed in the cytoplasm of a hepatocyte of some of the chimpanzees, but not observed in the cytoplasm of a hepatocyte of the other chimpanzees, and that an intranuclear particle is formed in the cytoplasm of a hepatocyte of some of the chimpanzees. These results and the results of the epidemiological observation and the tests on the presence or absence of the chloroform sensitivity suggest that a plurality of types of NANBV's exist, (see, for example, "Science", Vol. 205, pp. 197-200, 1979, and "Journal of Infectious Disease", Vol. 148, pp. 254-265, 1983). The amount of the NANBV present in the blood of a patient having NANB hepatitis is extremely small as compared to either the amount of a hepatitis A virus present in the feces of a patient having hepatitis A or the amount of a hepatitis B virus present in the blood of a patient having hepatitis B. For example, the amount of hepatitis B virus in the blood of the patient is $10^8$ to $10^9$ per ml in terms of Chimpanzee Infectious dose (CID), whereas the amount of NANBV in the blood of the patient is only $10^4$ to $10^5$ per ml in terms of CID (Bradley, D. W.: Research perspectives in post-transfusion non-A, non-B hepatitis, in "Infection, Immunity and Blood Transfusion", edited by Dodd, R. Y. & Barker, L. F., published by Alan R. Liss, Inc., New York (1985) pp. 81-97). Further, it is known that except for human, there are no animals except chimpanzee that are sensitive to NANBV and that in the cytoplasm of the hepatocyte, a typical tubular structure is occasionally formed by NANBV infection. Since only chimpanzee can be used as an animal for experiment of the NANBV infection, a large number of chimpanzees are required to be used for the study of NANBV. However, the chimpanzee is not easily available and expensive. Therefore, the study of NANBV by, for example, experimental infection by NANBV, identification of NANBV and search for a useful marker for NANBV, is necessarily restricted and delayed.

(3) Clinical observation: The latent period of the NANB hepatitis is 2 to 26 weeks. The symptom of NANB hepatitis in the early stage is mild as compared to that of hepatitis B. For example, a patient having NANB hepatitis only becomes feverish and complains of languor. Further, 70% of the patients have anicteric symptom. Therefore, the NANB hepatitis is frequently overlooked. However, the NANB hepatitis is very dangerous because the NANB hepatitis is likely to become chronic and, then, to progress to liver cirrhosis. That is, 40 to 50% of the patients having NANB hepatitis whose blood serum exhibits an increased aminotransferase activity develop chronic hepatitis. 10 to 20% of the cases of chronic hepatitis are accounted for by liver cirrhosis. Further, 0.5 to 1% of blood recipients per year become liver cirrhosis patients without subjective symptoms. Therefore, for preventing biohazard caused by concerned with blood transfusion and bleeding, eradication of the NANB hepatitis is a matter of global importance from the viewpoint of public health.

(4) Diagnosis: As mentioned above, the NANBV (blood-transmitted type) has not yet been identified and a viral marker, such as an NANBV antigen, useful for the diagnosis of NANB hepatitis has not been known. Therefore, diagnosis of NANB hepatitis has been conducted by examining the titer of the antibody in serum of a patient, which is specific for each of the known phlogogenic viruses, such as hepatitis A virus, hepatitis B virus, cytomegalovirus, EB virus, varicella virus and herpes simplex virus, and diagnosing the patient whose serum is negative with respect to the antibody specific for any of the above-mentioned viruses, as having NANB hepatitis. At the same time, another diagnosis method has also been used. For example, there have been used a method in which whether or not the activity of an enzyme in serum, such as GPT [glutamic-pyruvic transaminase, also known as "ALT" (alanine aminotransaminase)], GOT (glutamic-oxaloacetic transaminase, also known as "AST" (aspartate aminotransaminase)], and guanine deaminase (also known as "guanase") ("Kan-tan-sui (Liver, Gallbladder, Pancreas)", Vol. 14, pp. 519–522, 1987); a method in which guanase activity is determined based on the absorbance of a sample (Japanese Patent Application Laid-Open Specification No. 60-176600); and a method in which the activity of reverse transcriptase in blood is determined (U.S. Pat. No. 4,707,439). With respect to the GPT or GOT in serum mentioned above, standard for the diagnosis of NANB hepatitis in which lasting, abnormally high activities of GPT and GOT are utilized as a criterion for the diagnosis of NANB hepatitis, is employed in Japan ("Journal of Blood Transfusion Society in Japan", Vol. 31, No. 4, pp. 316–320, 1985). With respect to the diagnostic agent for NANB hepatitis, an antibody specifically reactive with an antigen which is formed in the blood of a patient having the symptoms of the NANB hepatitis is known. For example, a polyclonal antibody (Japanese Patent Application Laid-Open Specification No. 58-735), a monoclonal antibody (Japanese Patent Application Laid-Open specifications No. 58-183629, No. 61-561968 and No. 62-181798), a monoclonal antibody produced by a cell strain (Japanese Patent Application Laid-Open Specification No. 61-25484), an avidin-labeled antibody (Japanese Patent Application Laid-Open Specification No. 60-195454), and an antibody prepared from the serum of a monkey infected with an extract of a stool of a patient having NANB hepatitis (Japanese Patent Application Laid-Open Specification No. 62-249999) are known. Further, an NANB hepatitis-related antigen which is isolated and purified from anatomized liver of a patient having NANB hepatitis (Japanese Patent Application Laid-Open Specification No. 57-198867) has been reported. However, the diagnosis of NANB hepatitis has not been able to be attained accurately by the use of any of the above-mentioned methods, antibodies and antigen, because the enzymatic activity utilized as a criterion for the diagnosis of NANB hepatitis in the above-mentioned methods is not specific for the NANB hepatitis, and the antibodies and the antigen mentioned above are not specific for NANBV. Therefore, it has been desired to obtain a marker specific for NANBV.

(5) Therapy and Prevention: Recently, the therapeutic effect on chronic NANB hepatitis by the use of $\beta$-interferon has been attracting attention in the art ["Hepatology", Vol. 6, p. 117, 1986 (abstract)]. With respect to the dose of $\beta$-interferon and the period of administration, investigations have been made. However, the effectiveness of $\beta$-interferon has not yet been confirmed.

On the other hand, the various vaccines and diagnositic agents have been reported. For example, there can be mentioned an adjuvant vaccine containing an antigen derived from a serum of a patient having NANB hepatitis who has a symptom of a jaundice, which serum exhibits high GPT activity (Japanese Patent Application Laid-Open Specification No. 59-42455); an NANBV antigen specifically reactive with an antigen produced by a lymphocyte obtained from a patient having NANB hepatitis which lymphocyte has been transformed with EB virus which has been isolated and purified from cells of the liver of a chimpanzee having NANB hepatitis (Japanese Patent Application Laid-Open Specification No. 61-176856); a glycoprotein derived from a blood serum of a patient having NANB hepatitis (Japanese Patent Application Laid-Open Specification No. 62-30965); a DNA virus isolated from a blood serum of a patient having NANB hepatitis by affinity chromatography (Japanese Translation Publication No. 59-501774 of PCT Application Publication No. WO84/01107); an NANBV antigen isolated from the fibronectin fraction of blood plasma (Japanese Translation Publication No. 60-501241 of PCT Application Publication No. WO84/04326); a togavirus isolated from a serum and an urine of a patient having NANB hepatitis (U.S. Pat. No. 4,464,474); a vaccine containing, as an active ingredient, an NANBV surface antigen or a gamma globulin purified from a serum or a plasma of a patient having NANB hepatitis (U.S. Pat. No. 4,542,016); an NANBV purified from a serum of a patient having NANB hepatitis, and an antigen thereof (U.S. Pat. No. 4,673,634 and No. 4,702,909 and European Patent Application Publication No. 128,995); and an enterovirus-like virus isolated from an extract of a stool of a patient having NANB hepatitis (European Patent No. 71,640). However, since the NANBV have not yet been isolated, any confirmation cannot be made as to whether or not the above-mentioned vaccines and diagnostic agents are surely useful for specifically diagnosing and treating NANB hepatitis. Furthermore, with respect to the method for preventing an NANBV from spreading via blood preparation, there have been known, for example, a method in which a serum or a blood plasma is subjected to heat-treatment for 10 min at 60° C. (U.S. Pat. No. 4,438,098); a method in which freeze-dried blood preparations are prepared and subjected to heat-treatment (Japanese Patent Application Laid-Open Specification No. 59-110627); a method in which a fraction of a plasma protein precipitated from an organic solvent, such as chloroform, is collected and the organic solvent-soluble fraction containing the hepatitis viruses are discarded; and a method for the inactivation of NANBV by formalin (U.S. Pat. No. 4,291,020). However, as mentioned above, the NANBV has not yet been isolated and identified and, therefore, any confirmation cannot be made as to whether or not the blood treated by the above-mentioned methods is surely free from the NANBV. Therefore, the safety and effectiveness of the biological preparations obtained by the above-mentioned method are not insured. Accordingly, none of these methods have been put into practice use.

SUMMARY OF THE INVENTION

The present inventors have made extensive and intensive studies with a view toward solving the above-mentioned problems and developing an NANBV antigen. As a result, the present inventors have succeeded in cloning a cDNA coding for an NANBV antigen peptide having not only high reliability but also safety and effectiveness, directly from a plasma and a resected liver of a patient having NANB hepatitis, without multiplying the NANBV in a chimpanzee having unknown factors which are considered to have rendered difficult the isolation of NANBV, although the amount of NANBV in the plasma or the resected liver is extremely small, that is, as small as about 1/10,000 that of a hepatitis A virus or a hepatitis B virus. Thus, safe production of the NANBV antigen peptide with high purity on a large scale at low cost without biohazard, has for the first time been realized by expressing the cDNA coding for NANBV antigen peptide by means of recombinant DNA technique. Further, it has been found that the probe which is prepared from a cDNA library obtained from the RNA present in the plasma or resected liver derived from human can be specifically hybridized with the RNA in the plasma of a patient having NANB hepatitis patient by the Northern blot technique explained in Example 1. Further, it has been found that the thus obtained NANBV antigen peptide of the present invention exhibits antigen-antibody reaction with at least one of serum from a convalescent patient having acute NANB hepatitis and serum from a patient having chronic NANB hepatitis. Based on the above-mentioned findings, the present invention has been completed.

Therefore, it is an object of the present invention to provide an NANB hepatitis virus antigen peptide which is useful as an active ingredient for a diagnostic agent and a vaccine for NANB hepatitis.

It is another object of the present invention to provide a mixed peptide antigen comprising at least two NANBV antigen peptides.

It is still another object of the present invention to provide a cDNA coding for the NANBV antigen peptide which is useful as a diagnostic agent for NANB hepatitis.

It is a further object of the present invention to provide an effective method for the diagnosis of NANB hepatitis.

It is still a further object of the present invention to provide an effective method for screening blood for transfusion to select a blood free from NANBV.

BRIEF DISCUSSION OF THE DRAWINGS

In the Drawings:

FIG. 1 is an illustration of an autoradiogram obtained by subjecting sera to dot hybridization using, as a probe, a cDNA of the present invention labeled with $^{32}$P, in which specimens 1 to 5 are sera from patients having NANB hepatitis, specimens 6 and 7 are sera from patients having hepatitis B and specimen 8 is a serum from a healthy human who is diagnosed as negative to hepatitis; and FIGS. 2(a), 2(b), 2(c), 2(d), 2(e) and 2(f) individually show the nucleotide sequences of various cDNA's embodying the present invention.

DETAILED DESCRIPTION OF THE INVENTION

Figure 1:
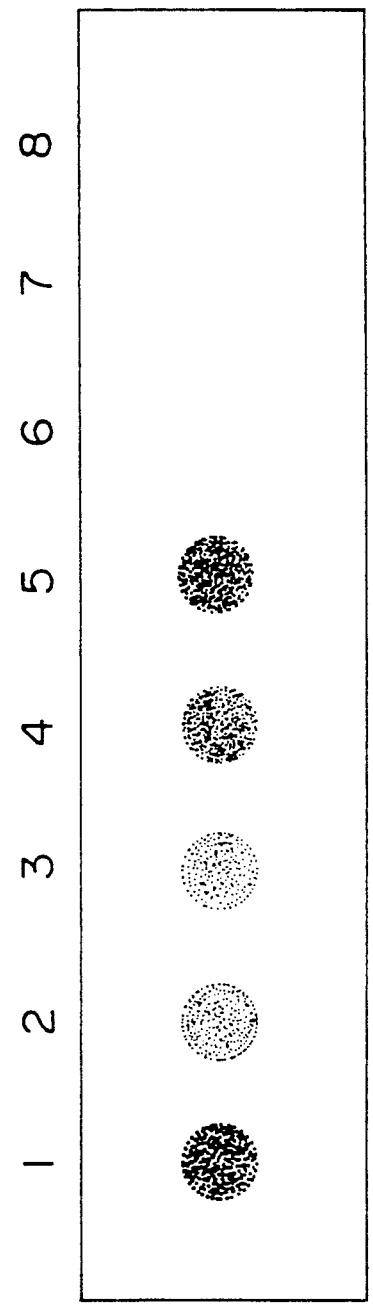

Essentially, according to the present invention, there is provided a non-A, non-B hepatitis virus antigen peptide which exhibits an antigen-antibody reaction with at least one member selected from the group consisting of serum from a convalescent patient having acute non-A, non-B hepatitis and serum from a patient having chronic non-A, non-B hepatitis, and which does not exhibit an antigen-antibody reaction either with serum from a human clinically diagnosed as negative to hepatitis or with serum from a patient having hepatitis diagnosed as other than non-A, non-B hepatitis.

Further, in another aspect of the present invention, there is provided a cDNA coding for a non-A, non-B hepatitis virus antigen peptide, said antigen peptide exhibiting an antigen-antibody reaction with at least one member selected from the group consisting of serum from a convalescent patient having acute non-A, non-B hepatitis and serum from a patient having chronic non-A, non-B hepatitis, and which does not exhibit an antigen-antibody reaction either with serum from a human clinically diagnosed as negative to hepatitis or with serum from a patient having hepatitis diagnosed as other than non-A, non-B hepatitis.

The NANBV antigen of the present invention is reactive with at least one of serum from a convalescent patient having acute NANB hepatitis and serum from a patient having chronic NANB hepatitis. That is, the NANBV antigen peptide of the present invention is reactive with only one of the serum from a convalescent patient having acute NANB hepatitis and the serum from a patient having chronic NANB hepatitis, or is reactive with either of these sera. However, the NANBV antigen peptide of the present invention does not exhibit an antigen-antibody reaction either with serum from a human clinically diagnosed as negative to hepatitis or with serum from a patient having hepatitis diagnosed as other than NANB hepatitis. As the hepatitis other than NANB hepatitis, hepatitis A, hepatitis B, a cytomegalovirus-caused hepatitis and an Epstein-Barr virus-caused hepatitis can be mentioned. A patient having acute or chronic NANB hepatitis is defined as a human diagnosed, as positive to NANB hepatitis, by exclusion of infection with known hepatitis viruses, including hepatitis A virus, hepatitis B virus, cytomegalovirus and Epstein-Barr virus according to the methods of Dienstag, J. L., "Non-A, non-B hepatitis. I. Recognition, epidemiology, and clinical features", Gastroenterology, 85, 439 (1983), and Dienstag, J. L., "Non-A, non-B hepatitis. II. Experimental transmission, putative virus agents and markers, and prevention", Gastroenterology, 85, 741 (1983). Whether the NANB hepatitis is acute or chronic can be determined by examining the liver tissue by biopsy according to the criterion described in Sheila Sherlock, Diseases Of The Liver And Biliary System, eighth edition, published by Blackwell Scientific Publications, London, 1989, pp. 326-333.

On the other hand, with respect to a patient having hepatitis A, to a patient having hepatitis B, to a patient having cytomegalovirus-caused hepatitis, to a patient having Epstein-Barr virus-caused hepatitis and to a healthy human, diagnoses can be made according to the above-mentioned methods of Dienstag.

The NANBV antigen peptide of the present invention can be obtained, for example, by gene expression of a DNA comprising at least one nucleotide sequence selected from the group consisting of formulae (I) to (VI):

(I)
GAATTCCAAAAAGAGCAAAACAAACCGCCGAAGAAA
AAACTAATAAGAGAAG
AAAAGGCGAAGAGACACAGGAAAAAAAAAACAGAGA
CGAAGGTCAGATAGAA
AAAAAGCAAGGAATTC;

(II)
GAATTCCGAGAACAAGACCAGATAAAAACCAAAGACA
GAACACAACAGAGAA
AGACGAAAAGAAGCACCAATCGCAGGCGAAGCAAAA
ACGAAAAAAAAAAAAA
AAAGGAATTC;

(III)
GAATTCCAAGAAAAAAGGGAGAAGCCAGCAATGGA
GAAGCCGAAAACGACA
CACACAAGAAACAAAGGAGGTACAAAGAAAAAGAAA
AAACGGCAACAAATAA
CCCAGGAAAGAACAAAAAGCCAAGAGTGGGCAGAAT
AAAAAACTGGAACCGG
GAGGGAAGGAAGGACGCATATCAGATTAGAAAAAGG
AGGGAATTC;

(IV)
GAATTCCTAAGAAATGGCTAGCCCTAGGAGAGGCAGT
CTTTCCCCAGTCAGT
TAGCCCGCAAATGCCAGAGCATCAAGAATTCAGAAAA
GGAGAAAATATAGTT
AATATCAAAGTGGTCGAAGCCTAAGATAGAGAGGTA
GAGAGTATGAAGAGTA
AGACGAATACAAACCAAAATTCTGGAATGATCATTAA
AAACATTATTGATAG
GTACTTAGAAGGGCAAGAGAGGAAGAAGAAAGTAAT
GAGAAATGCTTATGGA
AGCCAAAGGAGCTTTCCAGG
AGAAGAAAGGGAATTC;

(V)
GAATTCCCAACGCGTCGGCTTGGCCCGCGCCTTGGCC
GCCGACCCGCGCTGA
TGGCCGTGGAATTC;

(VI)
GAATTCCGGGGTATTTGCCTCGATCTGCCTGCTCAGC
GCTTCGGCCCTCGGC
TTGGGCGCCCTGCTGCTGGCTTCCGAGCAGCTATTCA
GCGCCTTGAAAGTGG
TTGGCGCGGCGTACGTGTCCGGGAATTC;

and nucleotide sequences individually obtained by substituting at least one nucleotide of each of said nucleotide sequences of formulae (I) to (VI) in accordance with degeneracy of genetic code.

In the above-mentioned formulae, A represents a deoxyadenylic acid residue, G a deoxyguanylic acid residue, C a deoxycytidylic acid residue and T a deoxythymidylic acid residue, and the left and right ends of each of formulae (I) to (VI) represent the 5'-hydroxyl group side and 3'-hydroxyl group side, respectively. The substitution of a nucleotide of each of the above-mentioned nucleotide sequences of formulae (I) to (VI) can be performed by the methods of, for example, Saiki et al., Science, 230, 1350-1354 (1985), and Saiki et al., Science, 239, 487-491 (1988).

Of the antigen peptides mentioned above, the antigen peptide obtained by gene expression of a DNA comprising a nucleotide sequence of formula (I) exhibits an antigen-antibody reaction with serum from a convalescent patient having acute NANB hepatitis. On the other hand, the antigen peptide obtained by gene expression of a DNA comprising a nucleotide sequence of formula (II) or (III) exhibits an antigen-antibody reaction with serum from a patient having chronic NANB hepatitis. Further, the antigen peptide obtained by gene expression of a DNA comprising a nucleotide sequence of formula (IV), (V) or (VI) exhibits an antigen-antibody reaction either with serum from a convalescent patient having acute NANB hepatitis or serum from a patient having chronic NANB hepatitis.

As is apparent from the above, the NANBV antigen peptide of the present invention is reactive with either the serum from a convalescent patient having acute NANB hepatitis or the serum from a patient having chronic NANB hepatitis, can easily be obtained by gene expression of a DNA comprising the nucleotide sequence of formula (IV), (V) or (VI). Alternatively, the NANBV antigen peptide which is reactive with either of the above-mentioned sera may be obtained by gene expression of a DNA prepared by ligating the nucleotide sequence of formula (I) to at least one of the nucleotide sequences of formulae (II) and (III). In this case, the NANBV antigen peptide of the present invention is a fused peptide comprising two or more of different antigen peptides The combination of nucleotide sequences contained in the DNA for obtaining the NANBV antigen peptide of the present invention is not restricted to the above-mentioned combination but any combination of at least two of the nucleotide sequences of formulae (I) through (VI).

Accordingly, in still another aspect of the present invention, there is provided a mixed antigen comprising at least two different non-A, non-B hepatitis antigen peptides.

Each of said different antigen peptides exhibits an antigen-antibody reaction with at least one member selected from the group consisting of serum from a convalescent patient having acute non-A, non-B hepatitis and serum from a patient having chronic non-A, non-B hepatitis, and does not exhibit an antigen-antibody reaction either with serum from a human clinically diagnosed as negative to hepatitis or with serum from a patient having hepatitis diagnosed as other than non-A, non-B hepatitis.

The NANBV antigen peptide of the present invention and the cDNA coding therefor may be prepared and identified by a process comprising steps of (1) to (8) described below.

Step (1): Selection and collection of a material for extracting an NANBV RNA

As a material for extracting the NANBV RNA, there may be used, for example, blood, lymph, ascites and hepatocyte of an NANBV carrier, or of a human or a chimpanzee suffering from NANB hepatitis. Since the materials derived from a chimpanzee may contain NANBV in a relatively small amount as compared to the materials derived from a human, the use of the materials derived from human is preferred. Of the blood, lymph, ascites and hepatocytes from a human, blood can most easily be obtained in a large amount. For example, blood which is not acceptable for use as a blood for transfusion is available from a blood bank in a large amount. Such blood can advantageously be used as a material for extracting an NANBV RNA. When blood is used as a material, blood is separated into plasma and erythrocytes. The thus obtained plasma is examined to determine whether or not the plasma is negative to the surface antigen of hepatitis B virus (WHO expert committee on viral hepatitis: Advances in viral hepatitis, WHO Technical Report Series, 602, 28-33, 1977) and negative to a genetic DNA of hepatitis B virus (Brechot, C., Hadchouel, M., Scotto, J., Degos, F., Charnay, P., Trepo, C., Tiollais, P.: Detection of hepatitis B virus DNA in liver and serum: a direct appraisal of the chronic carrier state. Lancet 2: 765-768, 1981). Further, the plasma is examined with respect to the activities of enzymes, such as GPT (Wrablewski, F. & LaDue, J. S.: Serum glutamic-pyruvic transaminase in cardiac and hepatic disease, Proc. Soc. Exp. Biol. Med., 91, 569, 1956), GOT, guanase and the like, which are employed as the criterion for the diagnosis of NANB hepatitis. The above-mentioned procedures of the separation of blood into plasma and erythrocytes and the examination of the plasma are conducted with respect to blood of different lots. The plasmas which are negative to both surface antigen and genetic DNA of hepatitis B virus and exhibit extremely high activities of the above-mentioned enzymes, for example, exhibit a GPT activity of 100 Karmen units or more, are pooled. With respect to the Karmen unit, reference may be made to Wrablewski, F. & LaDue, J. S.: Serum glutamic-pyruvic transaminase in cardiac and hepatic disease, Proc. Soc. Exp. Biol. Med., 91, 569, 1956.

The number of the NANB hepatitis virus in blood is extremely small as compared to that of the hepatitis B virus as mentioned hereinbefore. From the results of the infection experiment, the number of the NANB hepatitis virus in blood is estimated to be about 1/10,000 of the number of the hepatitis B virus (Bradley, D. W., (1985): Research perspectives in post-transfusion non-A, non-B hepatitis, in "Infection, Immunity and Blood Transfusion", edited by Dodd, R. Y. & Barker, L. F., published by Alan R. Liss, Inc., New York, pp. 81-97). Therefore, for the extraction of the RNA, it is preferred to use plasma in a large amount, for example, in an amount as large as about 30 to 100 l. When a hepatocyte is used as a material, 1 to 3 g of a non-cancerous portion of a liver tissue resected from a patient having hepatoma which is a complication of a chronic NANB hepatitis may advantageously be used.

Step (2): Preparation of the NANBV RNA

From the material obtained in Step (1), the RNA may be extracted and purified by conventional methods. For example, when plasma is used as the material for extracting the NANBV RNA, plasma is diluted with about 10 to 150 mM of a conventional buffer so that the final volume may become about 1.5 to 5 times the original volume. Then, the diluted plasma is used as an original solution for the extraction and purification of the RNA.

On the other hand, when a hepatocyte is used as a material for extracting the NANBV RNA, about 5 to 30-fold volume of a diluent containing ribonuclease inhibitor is added to the liver tissue. Then, according to the conventional method using a homogenizer and the like, the liver tissue is crushed or disrupted to obtain a homogenate of a hematocyte. Then, the homogenate is subjected to centrifugation to collect a supernatant. The collected supernatant is used as an original solution for the extraction and purification of the NANBV RNA. The extraction and purification of the RNA may be conducted by the conventional method, for example, an extraction method in which a mixture of a ribonuclease inhibitor, such as heparin, diethyl pyrocarbonate and guanidine thiocyanate, with a surfactant, a chelating agent, or a reducing agent capable of enhancing the denaturation of a protein, is used; a method in which fractionation is conducted by density gradient centrifugation using sucrose, cesium chloride, Ficoll (Pharmacia Fine Chemicals AB, Sweden) or the like as a solute of a gradient; a method in which separation is conducted by affinity column utilizing the 3'-terminal poly A chain which an mRNA specifically has; a separation method in which an RNA-bonded polysome is specifically obtained by the immunoprecipitation using an antibody specific for a protein synthesized on the polysome; a phenol extraction method based on a principle of two-phase separation; a precipitation method by the use of a polyethylene glycol, a dextran sulfate, an alcohol or the like. The above-mentioned methods may be used alone or in combination. The above-mentioned procedure for extracting and purifying the NANBV RNA may preferably be conducted at pH 3 to 10 in order to prevent the irreversible denaturation of the RNA.

Step (3): Preparation of a double-stranded cDNA from the NANBV RNA

Using the above-obtained NANBV RNA as a template, a cDNA may be prepared by a customary method. That is, using an oligodeoxythymidine and a hexanucleotide primer as primers, and using a reverse transcriptase, a cDNA complementary to the NANBV RNA is synthesized using the NANBV RNA as a template to obtain a double-strand comprising the cDNA and the NANBV RNA which are complementarily bonded to each other. Then, the thus obtained double-strand is reacted with ribonuclease H so that the NANBV RNA is decomposed and removed from the cDNA. Thus, a single-stranded cDNA is obtained. Using the obtained single-stranded cDNA as a template, a double-stranded cDNA is synthesized by a DNA synthase. The double-stranded cDNA synthesis may easily be conducted using a commercially available kit for cDNA synthesis, for example, cDNA Synthesis System Plus ® (manufactured and sold by Amersham International, England), cDNA System Kit ® (manufactured and sold by Pharmacia LKB, Sweden), cDNA Synthesis Kit ® (manufactured and sold by Boehringer Mannheim GmbH, West Germany), and the like.

Step (4): Confirmation of the specificity of the synthesized cDNA for the NANBV RNA In order to confirm the specificity of the synthesized cDNA for the NANBV RNA, the reactivity of the cDNA with a serum from a patient having NANB hepatitis was examined. The examination may generally be conducted using various hybridization techniques in combination. For example, the RNA's extracted from the plasma of an NANB hepatitis patient by the method as described in Step (2) are spotted on a nitrocellulose filter or a nylon filter. Then, the cDNA prepared in Step (3) is labeled with $^{32}P$, and the $^{32}P$-labeled cDNA is used as a probe for reacting with the RNA's spotted on the filter. The specificity of the synthesized cDNA for the NANBV RNA is determined based on the positive ratio of the dot-hybridization, i.e., the ratio of the number of the dotted RNA's which are hybridized with the labeled cDNA to the total number of the dotted RNA's.

The $^{32}P$-labeled DNA may be prepared as follows. The double-stranded cDNA prepared in Step (3) is subjected to thermal denaturation to obtain a single-stranded cDNA. Then, to the single-stranded cDNA is added a solution containing $^{32}P$-dCTP ($^{32}P$-labeled deoxycytidine 5'-triphosphate), dNTP (deoxyribonucleoside triphosphate) and Klenow fragment of a DNA polymerase. Then, the resultant mixture is incubated to thereby synthesize a $^{32}P$-labeled double-stranded cDNA.

The positive ratio with respect to the RNA's derived from the plasma of a healthy human and the positive ratio with respect to the RNA's derived from the plasma of a hepatitis B patient are 0% and about 0 to 3%, respectively. On the other hand, with respect to the RNA's derived from the plasma of a hepatitis NANB patient, the positive ratio is as high as about 30% or more, which means that the synthesized cDNA has a specificity for the NANBV RNA. This indicates that the double-stranded cDNA obtained in Step (3) has a nucleotide sequence corresponding to that of the NANBV RNA.

Step (5): Preparation of a cDNA library

Using the cDNA prepared in Step (3), a cDNA library is prepared by a customary method. That is, the cDNA prepared in Step (3) is cut into fragments having different lengths and the resultant various cDNA fragments are individually ligated to replicable cloning vectors, to thereby obtain a cDNA library. As a replicable cloning vector, any known or commercially available vectors, such as phage genes, cosmids, plasmids and animal virus genes may be used. When a phage gene or a cosmid is used as a replicable vector, in order to attain high stability and high transforming ability of the vector after each of the cDNA fragments has been individually inserted therein, the in-vitro packaging of each of the cDNA-inserted vectors is conducted by a customary method. Thus, the cDNA-inserted vectors are obtained in the form of a recombinant phage particle. The obtained phage particles are used as a cDNA library for cDNA cloning. On the other hand, when a plasmid is used as a replicable vector, each of the above-mentioned cDNA fragments is individually inserted in the plasmid vectors and the resultant cDNA-inserted vectors are then individually introduced into host cells, such as cells of *Escherichia coli, Bacillus subtilis*, yeast or the like, according to a customary method. The thus obtained transformants are used as a cDNA library for cDNA cloning. Further, when the animal virus gene is used as a replicable vector, each of the above-mentioned cDNA fragments is individually inserted in the virus gene vectors and the resultant recombinant viruses are then individually transfected into sensitive animal cells according to a standard method and multiplied in the cells. In the case of the recombinant virus, the obtained recombinant viruses as such are used as a cDNA library.

The preparation of the cDNA library may easily be conducted using a commercially available kit, for example, cDNA cloning system λgt10 and λgt11 (manufactured and sold by Amersham International, England; BRL Inc., U.S.A.; and Stratagene Inc., U.S.A.), in-vitro packaging system (manufactured and sold by Amersham International, England, and BRL Inc., U.S.A.) and the like.

Step (6): Cloning of a cDNA containing an NANBV gene from the cDNA library

In this step, a cDNA clone containing an NANBV gene is obtained. When the cDNA library is comprised of transformants, the transformants are cultured on a standard agar medium to form colonies. On the other hand, when the cDNA library is comprised of recombinant phage particles or recombinant viruses, these phage particles or recombinant viruses are used to infect known sensitive host cells, such as *Escherichia coli, Bacillus subtilis*, yeast, animal cell culture and the like, and cultured to form a plaque, or to multiply the infected cells. The above-obtained transformant colonies, plaques or infected cells are subjected to immunoassay by a standard method using a serum from a convalescent patient having acute NANB hepatitis and a serum from a patient having chronic NANB hepatitis individually, so that colonies, plaques or infected cells which have produced an NANBV antigen specifically reacted with at least one of the above-mentioned sera are selected and isolated. For the strict selection of the colonies, plaques and infected cells, it is preferred that the above procedure be repeated. From each of the thus selected and isolated colonies, plaques or the infected cells, a cDNA clone containing an NANBV gene is isolated according to a standard method described in T. Maniatis et al., Molecular Cloning, A Laboratory Manual, published by Cold Spring Harbor Laboratory, U.S.A., pp. 309-433 (1982).

The immunoassay may be conducted by, for example, an enzyme-labeled antibody technique in which an antibody labeled with an enzyme, such as peroxidase and alkaline phosphatase, is used; and a fluorescent antibody technique in which an antibody labeled with fluorescein isothiocyanate, europium or the like is used. It is preferred that the immunoassay by the above-mentioned technique be conducted by an indirect method because with the indirect method, high sensitivity immnoassay can be attained even by the use of an extremely small amount of a serum from a patient. As a primary antibody to be used in the indirect method, a serum from a patient having NANB hepatitis or a serum from a chimpanzee having NANB hepatitis may preferably be employed because these sera contain an antibody against an NANBV antigen in relatively large amount. As a secondary antibody to be used in the indirect method, a commercially available anti-human Ig antibody labeled with an enzyme, a fluorescent substance or the like may be used.

A specimen to be subjected to immunoassay may be prepared according to a conventional method, for example, a blotting method in which nucleic acids and proteins of the colonies, plaques and infected cells are adsorbed on a filter membrane, a method in which a microplate or a slide glass for microscopy is used, or the like. When the blotting method is used in combination with an indirect, enzyme-labeled antibody technique, the selection of the intended colonies, plaques or infected cells from an extremely large number of the original colonies, the original plaques or the original infected cells can be conducted easily and promptly. In this case, blotting is conducted by contacting a commercially available filter made of nitrocellulose, cellulose acetate, nylon or the like, with the colonies, the plaques or the infected cells.

In this step, it is preferred to determine the nucleotide sequence of each of the obtained cDNA clones. The determination of the nucleotide sequence of the cDNA clone may generally be conducted according to a conventional method, for example, the Maxam-Gilbert method, the dideoxy chain termination method (Analytical Biochemistry, 152, 232–238, 1986), or the like.

The cDNA clones are preferably classified into groups according to the respective properties of the NANBV antigen peptides coded for by the cDNA clones in order to identify clones from one another. In this connection, it has been found that some of NANBV's have an ability to cause a tubular structure to be formed in the cytoplasm of a hepatocyte of a chimpanzee, and some of NANBV do not have such an ability (Science, 205, 197–200, 1979). Therefore, the cDNA clones may be identified and classified by examining the serological reactivity of each cDNA clone with a serum from a chimpanzee infected with an NANBV of the type which causes a tubular structure to be formed in the cytoplasm of the hepatocyte of the chimpanzee, and a serum from a chimpanzee infected with an NANBV of the type which does not cause a tubular structure to be formed in the cytoplasm of the hepatocyte of the chimpanzee. The examination of this serological reactivity may be conducted by immunoassay mentioned above.

Step (7): Expression of the cDNA clone containing an NANBV gene and mass-production of an NANBV antigen peptide In order to express the cloned cDNA containing an NANBV antigen gene to produce an NANBV antigen peptide on a commercial scale, part or whole of the cloned cDNA present in the cDNA clone is taken out from the replicable cloning vector and recombined with a replicable expression vector. Illustratively stated, part or all of the cDNA of each cDNA clone is cut off using a restriction enzyme to obtain a DNA fragment containing an NANBV antigen gene (hereinafter referred to as "NANBV DNA fragment"). The NANBV DNA fragment is then inserted in a replicable expression vector by a customary method. When one DNA fragment is inserted in an expression vector, one type of antigen peptide can be produced by gene expression. When two or more of different DNA fragments are inserted in sequence in an expression vector, an antigen peptide can be produced by gene expression in the form of a fused peptide comprising peptides coded for by the inserted DNA fragments.

As the replicable expression vector which may be used in this step, any conventionally known or commercially available expression vector can be used. Examples of expression vectors include plasmid vector pSN508 for enterobacteria (U.S. Pat. No. 4,703,005), plasmid vector pBH103 for yeast, and its series (Japanese Patent Application Laid-Open Specification No. 63-22098), plasmid pJM105 (Japanese Patent Application Laid-Open Specification No. 62-286930), an attenuated chicken pox virus gene (Japanese Patent Application Laid-Open Specification No. 53-41202), an attenuated Marek's disease virus (The Journal of Japanese Society of Veterinary, 27, 20–24 (1974), and Gan Monograph on Cancer Research, 10, 91–107 (1971)), plasmid pTTQ series (manufactured and sold by Amersham International, England), plasmid pSLV series (manufactured and sold by Pharmacia LKB, Sweden), and the like.

The NANB DNA-inserted expression vectors are individually introduced or transfected into host cells sensitive to the vector according to a conventional method, to obtain transformants. Then, from the transformants, the transformant(s) which has produced an NANBV antigen peptide is selected. The production of an NANBV antigen peptide may be detected by the immunoassay mentioned above in Step (6). When an animal virus gene is used as an expression vector, a recombinant virus having an NANBV antigen peptide on the surface thereof may be obtained. Such a recombinant virus may advantageously be used as a raw material for a multifunctional vaccine having not only an antigenicity inherent in the virus vector but also an antigenicity of the NANBV.

By culturing the transformant or the recombinant virus obtained above according to a customary method, an NANBV antigen peptide can be produced in the culture of the transformant or the recombinant virus on a commercial scale.

Step (8): Purification of an NANBV antigen peptide

The NANBV antigen peptide produced in the culture of the transformant or recombinant virus may be purified using an appropriate combination of customary techniques selected from, for example, salting-out; adsorption and desorption using a silica gel, an activated carbon or the like; precipitation by an inorganic solvent; fractionation by ultracentrifugation; ion exchange chromatography; affinity chromatography; high-performance liquid chromatography; electrophoresis, and the like.

When the NANBV antigen peptide is purified from the culture of an *E. coli* transformant or a yeast transformant, from a viewpoint of the effective removal of allergens derived from *E. coli* and yeast which cause the quality of the final product of the NANBV antigen peptide to be markedly lowered, it is preferred that the purification be conducted by, for example, the steps of adsorption and elution using a silica gel, removal of impurities by adsorption on an activated carbon, and density gradient centrifugation in this order (Japanese Patent Application Laid-Open Specification No. 63-297). When the NANBV antigen peptide is purified from the culture of a recombinant virus, e.g., the culture of a recombinant virus-infected cells, a high purity NANBV antigen peptide can be obtained by subjecting a crude solution containing the antigen peptide to purification by ultracentrifugation and density gradient centrifugation repeatedly.

Thus, a solution containing a purified NANBV antigen peptide of the present invention is obtained. If desired, the solution may be lyophilized to obtain a purified NANBV antigen peptide in a dry form.

The mixed peptide antigen of the present invention may be obtained by mixing at least two different types of the NANBV antigen peptides obtained by gene expression of at least two different types cDNA's having different nucleotide sequences.

The purified NANBV antigen peptide of the present invention is useful as a diagnostic agent for diagnosing NANB hepatitis. Accordingly, in still a further object of the present invention, there is provided a method of diagnosing non-A, non-B hepatitis, which comprises:

contacting serum from an unknown patient with a non-A, non-B hepatitis virus antigen peptide which peptide exhibits an antigen-antibody reaction with at least one member selected from the group consisting of serum from a convalescent patient having acute non-A, non-B hepatitis and serum from a patient having chronic non-A, non-B hepatitis, and does not exhibit an antigen-antibody reaction either with serum from a human clinically diagnosed as negative to hepatitis or with serum from a patient having hepatitis diagnosed as other than non-A, non-B hepatitis;

determining whether said serum reacts with said non-A, non-B hepatitis virus antigen peptide; and classifying said serum as positive or negative to non-A, non-B hepatitis based on said reactivity.

The contact of serum from a patient with the NANBV antigen peptide of the present invention may be conducted in substantially the same manner as described in Step (6) mentioned above, except that a serum from a patient who is not determined as to whether or not the patient is an NANB hepatitis patient is used instead of the serum from a patient having NANB hepatitis.

The NANBV antigen peptide of the present invention for use in the above-mentioned method may be prepared as follows. The purified NANBV antigen peptide solution in Step (8) mentioned above is put in a vessel such as a vial and an ampul and sealed. The antigen peptide solution put in a vessel may be lyophilized before sealing in the same manner as mentioned above. The amount of the NANBV antigen peptide put in a vessel is generally about 1 μg to about 10 mg. Alternatively, the NANBV antigen peptide may also be adsorbed on the surface of a customarily used support, such as a microplate, polyethylene beads, filter paper or a membrane.

The determination of the reactivity of the serum with the NANBV antigen peptide may be conducted in substantially the same manner as described in Step (6) mentioned above. That is, the determination of the reactivity may be conducted by a conventional immunoassay method, such as radioimmunoassay (RIA), enzyme-linked immunosorbent assay (ELISA), fluorescent antibody technique (FA), passive haemagglutination (PHA), reversed passive haemagglutination (rPHA) and the like. The amount of the NANBV antigen peptide to be used for the above immunoassay is generally from about 0.1 to about 100 mg/ml of serum. Particularly, the amounts of the NANBV antigen peptide to be used for RIA, ELISA, FA, PHA and rPHA are generally from 0.1 to 1 mg/ml, from 0.1 to 1 mg/ml, from 1 to 100 mg/ml, from 1 to 50 mg/ml and from 1 to 50 mg/ml, respectively.

The NANBV antigen peptide of the present invention may also be used for screening blood for transfusion. Accordingly, in still a further aspect of the present invention, there is provided a method for screening a blood for transfusion, comprising:

a) isolating serum from whole blood;

b) contacting a serum of an unknown blood with non-A, non-B hepatitis virus antigen peptide which exhibits an antigen-antibody reaction with at least one member selected from the group consisting of serum from a convalescent patient having acute non-A, non-B hepatitis and serum from a patient having chronic non-A, non-B hepatitis, and does not exhibit an antigen-antibody reaction with serum from a human clinically diagnosed as negative to hepatitis and with serum from a patient having hepatitis diagnosed as other than non-A, non-B hepatitis;

c) determining whether said serum reacts with said non-A, non-B hepatitis virus antigen peptide;

d) classifying said serum as positive or negative to non-A, non-B hepatitis based on said reactivity; and e) effecting separation of the blood in accordance with said identification.

The contact of serum of an unknown blood with the NANBV antigen peptide of the present invention, and the determination of the reactivity of the serum of the blood with the NANBV antigen peptide may be conducted in the same manner as mentioned above with respect to the method for diagnosing NANBV antigen peptide. By the present method, a blood for transfusion free from the NANBV can be selected.

Further, the NANBV antigen peptide of the present invention may advantageously be used as an active ingredient of a vaccine for NANB hepatitis. The vaccine for NANB hepatitis may be prepared as follows. The culturing of a transformant containing a recombinant phage or plasmid carrying the cDNA coding for the NANBV antigen peptide, or a cell infected with the recombinant virus carrying the cDNA coding for the NANBV antigen peptide is conducted in the same manner as described above to produce the NANBV antigen peptide in the culture. For detoxifying the NANBV antigen peptide in the culture to secure the safety of the antigen peptide and for fixing the antigen peptide to stabilize the immunogenicity and the antigenicity of the antigen peptide, it is preferred to add a conventional inactivating agent to the culture of the transformant or recombinant virus-infected cell, or to a culture medium obtained by removing the transformant cells or the recombinant virus-infected cell. For example, an inactivating agent, such as formalin, may be added in an amount of from 0.0001 to 0.001 v/v %, followed by incubation at 4° to 37° C. for 5 to 90 days. Then, the resultant culture or culture medium is subjected to purification in the same manner as mentioned above. Thus, an original NANB hepatitis vaccine solution containing the purified NANBV antigen peptide is obtained.

The original NANBV hepatitis vaccine solution is filtered using a microfilter by a standard method to sterilize the solution. The filtrate is diluted with physiological saline so that the protein concentration is about 1 to about 500 µg/ml as measured by the Lowry method. To the resultant solution is then added aluminum hydroxide gel as an adjuvant so that the concentration of the added gel becomes about 0.1 to about 1.0 mg/ml. As an adjuvant, there may also be employed precipitating depositary adjuvants such as calcium phosphate gel, aluminum phosphate gel, aluminum sulfate, alumina and bentonite, and antigen-production inducing adjuvants such as muramyl peptide derivatives, polynucleotides, Krestin ® (manufactured and sold by Kureha Chemical Industry Co., Ltd., Japan) and picibanil (both of which are an antineoplastic agent). Further, to the mixture, at least one stabilizing agent may be added. As the stabilizing agent, any commercially available stabilizing agent may be used. Examples of stabilizing agents include gelatin and hydrolysates thereof, albumin, succharides such as glucose, fructose, galactose, sucrose and lactose, and amino acids such as glycine, alanine, lysine, arginine and glutamine.

Then, the thus obtained NANB hepatitis vaccine solution containing a gel-adsorbed NANBV antigen peptide is separately poured into a small vessel, such as an ampul and a vial, and sealed. Thus, there is obtained a purified adsorbed NANB hepatitis vaccine comprising an adsorbed NANBV antigen peptide.

The NANB hepatitis vaccine solution thus obtained may be lyophilized to obtain the NANB hepatitis vaccine in a dried form so that the product can be transported to and stored at a place of severe atmosphere, for example, in an area in the tropics. The lyophilization may generally be conducted according to a standard method after the liquid adsorbed NANB hepatitis vaccine is put in a vessel such as a vial and an ampul. After lyophilization, a nitrogen gas is introduced in the vessel containing the dried vaccine, followed by sealing. Incidentally, the quality of the vaccine produced is examined in accordance with "Adsorbed Hepatitis B Vaccine", "Dried Japanese Encephalitis Vaccine", and "Adsorbed Pertussis Vaccine" provided for in Notification No. 159 of the Ministry of Health and Welfare, Japan, "Minimum Requirements for Biological Products".

The NANB hepatitis vaccine may be prepared in the form of a mixed vaccine which contains an adsorbed NANBV antigen peptide mentioned above and at least one antigen other than the present NANBV antigen peptide. As the antigen other than the present NANBV antigen peptide, there may be employed any antigens that are conventionally used as active ingredients of the corresponding vaccines insofar as the side effects and adverse reactions caused by such other antigens and the NANBV antigen peptide are not additively or synergistically increased by the use of the NANBV antigen peptide and such other antigens in combination and the antigenicities and immunogenicities of the NANBV antigen peptide and such other antigens are not reduced by the interference between the NANBV antigen peptide and other antigens. The number and the types of the antigens which may be mixed with the NANBV antigen peptide are not limited insofar as the side effects and adverse reactions are not increased additively or synergistically and the antigenicity and immunogenicity of each of the NANBV antigen peptide and such antigens are not reduced as mentioned above. Generally, two to six types of antigens may be mixed with the NANBV antigen peptide. Examples of antigens which may be mixed with the present NANBV antigen peptide, include detoxified antigens, inactivated antigens or toxoids which are derived from Japanese encephalitis virus, HFRS (hemorrhagic fever with renal syndrome) virus, influenza virus, parainfluenza virus, hepatitis B virus, dengue fever virus, AIDS virus, *Bordetella pertussis*, diphtheria bacillus, tetanus bacillus, meningococcus, pneumococcus and the like.

Generally, the vaccine comprising the NANBV antigen peptide of the present invention may be contained and sealed in a vial, an ampul or the like. The vaccine of the present invention may generally be administered in the form of a liquid or suspension. In the case where the vaccine is in a dried form, the vaccine is dissolved or suspended in sterilized distilled water before administration, the amount of the distilled water being such that the volume becomes the original volume before being subjected to lyophilization. Generally, the vaccine may be administered subcutaneously. The dose of the vaccine per person may generally be about 0.5 ml. In general, the dose of the vaccine per child may be half as much as that of the vaccine per adult. The vaccine may generally be administered twice at an interval of about one week to one month and then, about half a year later, administered once more.

Further, the NANBV antigen peptide may be used for preparing an antibody, such as a polyclonal antibody and a monoclonal antibody, specific for the NANBV antigen peptide. For example, a polyclonal antibody specific for the NANBV antigen peptide may be prepared by a conventional method as follows. The purified NANBV antigen peptide of the present invention is inoculated subcutaneously, intramuscularly, intraperitoneally or intravenously to an animal, such as mouse, guinea pig and rabbit. The inoculation of the NANBV antigen peptide is generally conducted several times at intervals of 1 to 4 weeks, to thereby completely immunize the animal. In order to enhance the immunizing effect, a conventional and commercially available adjuvant may be used. Then, blood serum is collected from the immunized animal and an anti-NANBV antigen peptide polyclonal antibody is isolated and purified from the blood serum according to a standard method.

On the other hand, a monoclonal antibody specific for the NANBV antigen peptide may be prepared by a conventional method as described in, for example, Cell Technology, 1, 23-29 (1982). For example, the splenic cells obtained from a mouse immunized with the purified NANBV antigen peptide are fused with commercially available mouse myeloma cells by cell fusion technique, to obtain hybridomas. The hybridomas are screened to obtain a hybridoma capable of producing an antibody reactive with the NANBV antigen peptide. The obtained hybridoma is cultured in a standard method. From the supernatant of the culture, an anti-NANBV antigen peptide monoclonal antibody is isolated and purified by a standard method.

The above-mentioned polyclonal antibody and monoclonal antibody may also be used as a diagnostic agent for diagnosing NANB hepatitis. The diagnosis of NANB hepatitis using the antibody may be conducted by immunoassay in substantially the same manner as mentioned above with respect to the diagnosis of NANB hepatitis using the NANBV antigen peptide. By the use of the polyclonal antibody or the monoclonal antibody, the identification and quantification of the NANBV antigen peptide present in a liver tissue and blood can be conducted.

The cDNA of the present invention coding for the NANBV antigen peptide may also be used for diagnosing NANB hepatitis by hybridization technique. That is, the cDNA coding for the NANBV antigen peptide is labeled with, for example, biotin, alkaline phosphatase, radioisotope $^{32}P$ or the like and used as a probe for hybridization. The cDNA to be used for the diagnosis may be prepared by a standarad method, for example, as follows. The recombinant phage containing the NANBV cDNA obtained in Step (6) mentioned above is digested with an appropriate restriction enzyme to cut off the DNA fragment containing the NANBV cDNA. The obtained DNA fragment is ligated to a commercially available replicable cloning plasmid to obtain a recombinant plasmid containing the DNA fragment. The recombinant plasmid is introduced in a host cell to form a transformant and the transformant is cultured to multiply the recombinant plasmid. The multiplied recombinant plasmid is isolated from the transformant and digested with a restriction enzyme. The resultant digest is subjected to low-meling point agarose gel electrophoresis to isolate and purify the cDNA coding for the NANBV antigen peptide. The thus obtained cDNA is labeled with biotin, alkaline phosphatase, radioisotope $^{32}P$ or the like. The labeling of the cDNA may be conducted by using a commercially available nick translation kit or multiprime kit (manufactured and sold by, for example, Amersham International, England; Nippon Gene Co., Ltd., Japan; and the like). The labeled cDNA is put in a vessel, such as a vial or an ampul, and sealed. The amount of the labeled cDNA put in a vessel is generally 1 to 100 µg per vessel. The labeled cDNA may be contained in the vessel in the form of a solution. Alternatively, the labeled cDNA may be contained in the vessel in a lyophilized state. The diagnosis of NANB hepatitis by the use of the labeled cDNA is conducted by a standard hybridization method. That is, a plasma, a serum or leukocytes obtained from a patient is placed in contact with the labeled cDNA and an RNA hybridized with the labeled cDNA is detected. The detection of the RNA hybridized with the labeled cDNA may be conducted by a standard method. When the cDNA is labeled with an enzyme, the detection is conducted by enzyme immunoassay. When the cDNA is labeled with a radioisotope, the detection is conducted by, for example, scintillation counting.

The NANBV antigen peptide of the present invention is specifically reactive with the NANBV. Therefore, when the NANBV antigen peptide is used as a diagnostic agent, the diagnosis of NANB hepatitis can be conducted easily with high reliability. Further, when the NANBV antigen peptide of the present invention is used for screening blood for transfusion, blood which is infected by NANBV can be selected easily with high reliability and removed from blood not infected by NANBV. Therefore, the post-transfusion NANB hepatitis can be prevented.

Further, the NANBV antigen peptide of the present invention may advantageously be used as an active ingredient of a vaccine for preventing NANBV hepatitis.

Further, by the use of the NANBV antigen peptide of the present invention, an antibody, particularly monoclonal antibody, specific for NANBV can easily be prepared. The antibody specific for NANBV can advantageously be used as not only a diagnostic agent for diagnosing NANB hepatitis, but also an active ingredient of a vaccine for treating NANB hepatitis.

Further, the NANBV antigen peptide of the present invention is not produced by the infection of an animal with a virus, but produced by gene expression of the DNA coding for the present antigen peptide in a host cell. Hence, the possibility of infection during the steps for production of the present antigen peptide is substantially eliminated. Also, the production cost can be decreased. Moreover, since all of the materials used in the production process, e.g., medium for the incubation system, are well-known in respect of the composition and construction thereof, purification is facile and an antigen peptide product having high purity can be obtained.

The present invention will now be described in detail with reference to the following Examples, which should not be construed to be limiting the scope of the present invention.

EXAMPLE 1

Step 1 (Extraction of a plasma RNA for preparing cDNA)

To 70 l of plasma which has a GPT activity of 100 Karmen/l or more (as measured by the method of Wroblewski, F. & LaDue, J. S.: Serum glutamic pyruvic transaminase in cardiac and hepatic disease, Proc. Soc. Exp. Biol. Med., 91: 569, 1956) and is negative to the surface antigen and DNA of hepatitis B virus (as measured by the method of Brechot, C., Hadchouel, M., Scotto, J., Degos, F., Charnay, P., Trepo, C., Tiollais, P.: Detection of hepatitis B virus DNA in liver and serum: a direct appraisal of the chronic carrier state, Lancet 2: 765-768, 1981) was added an equal volume of an aqueous diluent containing 50 mM Tris-HCl and 1 mM EDTA (pH 8.0). The resultant mixture was subjected to continuous flow centrifugation at 7,400×g, 4° C. at a flow rate of 300 ml/min to obtain a supernatant. The supernatant was subjected to sucrose density gradient centrifugation using a sucrose density gradient of 0 to 60% (w/v), at 90,000×g, 4° C. at a flow rate of 100 ml/hour by means of a zonal centrifuge (manufactured and sold by Electro Nucleonics, U.S.A.) to conduct the fractionation of the supernatant. Thus, there were obtained a precipitate fraction, a first fraction containing substances of a specific gravity of 1.17 to 1.29, a second fraction containing substances of a specific gravity of 1.12 to 1.17 and the uppermost fat-containing layer as a third fraction. Each of the fractions was subjected to dialysis against a solution containing 25 mM Tris-HCl (pH 8.0) and 0.5 mM EDTA to remove the sucrose. After lyophilizing each of the dialyzed fractions, each of the fractions was dissolved in 20 ml of a solution containing 4M guanidine thiocyanate, 20 mM sodium citrate (pH 7.0), 0.5% sarcosine and 0.1M 2-mercaptoethanol (RNA Solution A).

In order to extract RNA, 1/10 volume of 2M acetic acid buffer (pH 4.1) was added to the above-obtained RNA solution A and, further added 300 µg of a poly C (manufactured and sold by P-L Biochemicals Co., Ltd., Sweden) as a carrier RNA. To the mixture was added a phenol containing chloroform and isoamyl alcohol to extract a nucleic acid in an aqueous layer. To the thus obtained aqueous layer was added an equal volume of isopropanol to precipitate the nucleic acid. The obtained precipitate was dissolved in 2M acetic acid buffer (pH 4.1) containing 0.2 ml of 4M guanidine thiocyanate. Then, an equal amount of isopropanol was added to the resultant buffer solution to precipitate the nucleic acid. The resultant precipitate was stored at −70 °C. in 75 w/w % ethanol.

Further, in order to remove a DNA which was copresent together with the nucleic acid, the nucleic acid was treated with a deoxyribonuclease (DNase) (manufactured and sold by Promega Biotex, U.S.A.) which had been subjected to affinity chromatography using a column packed with 5'-(4-aminophenylphosphoryl)-uridine-2'(3')-phosphate agarose (manufactured and sold by Promega Biotex, Miles-Yeda Lab., U.S.A.) to completely remove rebonuclease (RNase) therefrom. Thus, the co-present DNA was digested and removed. Further, for removing the poly C added as a carrier RNA from the nucleic acid, the nucleic acid was subjected to affinity chromatography using oligo (dG) cellulose column (manufactured and sold by Pharmacia Fine Chemicals AB, Sweden, type 7, 2 gm) to obtain a fraction containing the nucleic acid. Then, the obtained fraction was applied to a column packed with NEN-SORB (manufactured and sold by E.I. DuPont De Nemours and Company, U.S.A.) and lyophilized, to thereby obtain a purified RNA.

Step 2 (Preparation of a double-stranded cDNA)

A double-stranded cDNA was prepared from the above-obtained RNA using a commercially available cDNA synthesis kit (manufactured and sold by Amersham International, England). Illustratively stated, 1 μg of the purified RNA prepared in Step 1 of Example 1 and 8 μl of a standard solution attached to the kit were put in a reaction tube. Then, to the mixture was added an oligo (dT) primer, 20 μCi of ($\alpha$-$^{32}$P)dCTP and 20 units of a reverse transcriptase. Then, the above-mentioned standard solution was added to the mixture in an amount such that the total volume of the resultant mixture became 20 μl. The mixture was incubated at 42° C. for 40 min to advance a reaction. Then, the reaction tube containing the mixture was cooled in ice water. For synthesizing the second cDNA strand, to the mixture in the reaction tube cooled in ice water were added 37.5 μl of a buffer for the double-stranded cDNA synthesis, which is attached to the kit, 20 μCi of ($\alpha$-$^{32}$P)dCTP, 0.8 unit of *Escherichia coli* ribonuclease H and 23 units of *Escherichia coli* DNA polymerize I. Then, distilled water was added to the mixture in an amount such that the total volume of the resultant mixture became 100 μl. The thus obtained mixture was incubated at 12° C. for 60 min and, then, incubated at 22° C. for 60 min and further incubated at 70° C. for 10 min. To the resultant mixture were added 2 units of T4 DNA polymerase and the mixture was incubated at 37° C. for 10 min to advance a reaction. Then, 4 μl of a 0.25M aqueous EDTA (pH 8.0) was added to the resultant mixture to terminate the reaction.

To 104 μl of the above-obtained reaction mixture was added an equivolume of a mixture of phenol and chloroform (1:1, v/v) and sufficiently mixed together. The mixture is then centrifuged at 10,000 rpm for 1 min and an aqueous layer was collected. To the above-obtained aqueous layer, a mixture of phenol and chloroform was added and centrifuged in the same manner as mentioned above to obtain an aqueous layer. Then, an equivolume of chloroform was added to the aqueous layer and sufficiently mixed together, followed by centrifugation for several seconds to obtain an aqueous layer. To the obtained aqueous layer was added an equivolume of 4M aqueous ammonium acetate and further added a 2-fold volume of cold ethanol (−20° C.) to form a cDNA precipitate. The mixture was then centrifuged at 15,000 rpm for 10 min to collect the precipitate. The thus obtained precipitate was dissolved in 50 μM of 2M aqueous ammonium acetate. 100 μl of cold ethanol was added to the solution to precipitate a cDNA, followed by centrifugation to collect the precipitate. The collected precipitate was dried and dissolved in 20 μl of a TE buffer containing 10 mM Tris-HCl (pH 8.0) and 0.1 mM EDTA, and stored at −20° C. The precipitate comprises a plurality of cDNA's complementary to different portions of the RNA obtained in Step 1 of Example 1.

Step 3 (Preparation of $^{32}$P-labeled cDNA probes)

25 ng of the cDNA precipitate prepared in Step 2 of Example 1 was heated at 100° C. for 5 min and immediately cooled, to thereby form a single-stranded DNA. To the single-stranded DNA were added 20 μg of bovine serum albumin, 50 Ci of $^{32}$P-dCTP (3000 Ci/mmol), 1 mmol dNTP (not containing dCTP), 5 μg of a random hexanucleotide and 2 units of a DNA polymerase I (Klenow fragment) and the total volume of the resultant mixture was adjusted to 50 μl by the addition of a TE buffer. The resultant mixture was incubated at 42° C. for 20 min to advance a reaction, and immediately applied to a column packed with Sephadex G50 (manufactured and sold by Pharmacia Fine Chemicals AB, Sweden) to thereby remove an unreacted $^{32}$P-dCTP. Thus, $^{32}$P-labeled cDNA probes were obtained.

Step 4 (Detection of NANBV nucleic acid by dot hybridization)

Using sera from healthy human adults (10 samples), sera from patients having hepatitis B (20 samples) and sera from patients having NANB hepatitis (60 samples), whether or not the nucleic acid of the NANBV in the serum can be detected using the $^{32}$P-labeled cDNA probes obtained in Step 3 of Example 1 was examined by dot hybridization as follows.

10 ml of each serum was added an equivolume of a diluent containing 50 mM Tris-HCl (pH 8.0) and 0.1 mM EDTA, and subjected to centrifugation at 100,000×g for 6 hours to thereby obtain a precipitate. The thus obtained precipitate was dissolved in 0.2 ml of a solution containing 4M guanidine thiocyanate mentioned in Step 1 of Example 1. To the resultant solution were added 8 μg of poly C and 20 μl of 2M aqueous sodium acetate (pH 4.1), followed by phenol extraction and isopropyl alcohol precipitation to obtain a precipitate. The thus obtained precipitate was dissolved in the above-mentioned solution containing 4M guanidine thiocyanate, followed by isopropyl alcohol precipitation to obtain a precipitate. The thus obtained precipitate was dissolved in 0.2 ml of a TE buffer containing 10 mM Tris-HCl (pH 8.0) and 0.1 mM EDTA. Further, the resultant solution was passed through the above-mentioned oligo(dG) column and NENSORB column successively, and to the resultant eluate was added formamide so that the formamide concentration of the resultant addition became 15% by weight and, further added an equivolume of 20×SSC solution (3M sodium chloride and 0.3M sodium citrate). The thus obtained mixture was heated at 50° C. for 15 min and immediately cooled in ice. The resultant mixture was spotted on BIODAIN nylon filter (manufactured and sold by Pall Co., U.S.A.). Then, the nylon filter was subjected to baking at 80° C. for 2 hours. The resultant filter was treated with a prehybridization solution containing 50 w/w % formamide, 5×SSC, 5×Denhart, 50 mM phosphate-citrate buffer (pH 6.5), 1 w/w % glicine and 100 µg/ml salmon sperm DNA at 42° C. for 6 hours and the solution was discarded. On the other hand, the $^{32}$P-labeled cDNA probes prepared in Step 3 of Example 1 was added to a prehybridization solution as mentioned above. The above-obtained filter was put into the above-obtained prehybridization solution containing the $^{32}$P-labeled cDNA probes and incubated at 42° C. for 22 hours to conduct hybridization. Then, the resultant filter was washed with a 2×SSC solution containing 0.1% SDS four times and, further washed with a 0.1×SSC solution containing 0.1% SDS twice. The washed filter was dried and subjected to autoradiography to determine whether a nucleic acid hybridized with $^{32}$P-labeled cDNA probes is present (positive) or not (negative). The results are shown in Table 1. The results show that by the use of the cDNA probes, i.e., the $^{32}$P-labeled cDNA probes prepared from the purified RNA of Step 1 of Example 1, the nucleic acid of the NANBV was specifically detected at high positive ratio (the ratio of the number of positive samples to the number of samples examined).

TABLE 1

| | The number of samples examined | The number of positive samples | Positive ratio (%) |
| --- | --- | --- | --- |
| Healthy human adult | 10 | 0 | 0 |
| Patient having hepatitis B | 20 | 1 | 5 |
| Patient having NANB hepatitis | 60 | 24 | 40 |

Step 5 (Preparation of a cDNA library using λgt11 phage)

Using a commercially available cDNA cloning kit (manufactured and sold by Amersham International, England), the cDNA library was prepared as follows.

(i) Preparation of EcoRI linker-tailed cDNA's

To 200 ng of the cDNA precipitate prepared in Step 2 of Example 1 was added 4 µl of a M-buffer and 2 µl of 1×SAM solution, both of which were provided with the above-mentioned kit. Then, distilled water was added to the above-obtained solution so that the total volume of the resultant solution became 20 µl. To the thus obtained solution was added 4 units of EcoRI methylase and incubated at 37° C. for 60 min. Then, the resultant reaction solution was heated at 70° C. for 10 min to form a methylated cDNA. For adding an EcoRI linker to the ends of the methylated cDNA, 3 µl of L-buffer and 2 µl of EcoRI linker, both of which were attached to the kit, were added to the above-obtained solution containing the methylated cDNA. Then, distilled water was added to the solution so that the total volume of the resultant solution became 30 µl. To the solution were added 5 units of T4 DNA ligase and the mixture was incubated at 15° C. for 18 hours. The resultant solution was heated at 70° C. for 10 min to inactivate the ligase. Further, 10 µl of E-buffer attached to the kit was added to the solution and distilled water was added so that the total volume of the resultant solution became 100 µl. To the solution, 100 units of a restriction enzyme EcoRI were added and the mixture was incubated at 37° C. for 5 hours to advance a reaction. Then, the reaction mixture was heated at 70° C. for 10 min to terminate the reaction. For removing the surplus of the EcoRI linker remaining unreacted, the obtained solution was applied to a column attached to the kit and a fraction containing the cDNA was collected. To the fraction was added 1/10 volume of 3M aqueous sodium acetate and 2.5-fold volume of cold ethanol, and the resultant mixture was cooled at −20° C. to precipitate the EcoRI-tailed cDNA's. The precipitated cDNA's were collected and dissolved in STE-buffer provided with the kit at a cDNA concentration of about 50 ng/µl.

(ii) Insertion of the EcoRI linker-added cDNA to λgt11 phage

To 50 ng of the EcoRI linker-tailed cDNA's were added 2 µl of a λgt11 arm DNA and 1 µl of L-buffer, both of which were provided with to the kit. Then, distilled water was added to the mixture so that the total volume of the resultant solution became 10 µl. Further, 2.5 units of T4 DNA ligase were added to the mixture, followed by incubation at 15° C. for 18 hours to thereby prepare recombinant λgt11 DNA's.

(iii) In-vitro packaging of the recombinant λgt11 DNA

To the solution containing the recombinant λgt11 DNA's prepared above were added 10 µl of solution (A) and 15 µl of solution (B), both of which were provided with the kit, and the mixture was incubated at 20° C. for 2 hours to form recombinant phages. To the resultant mixture was added 0.5 ml of SM-buffer provided with the kit and, further added 10 µl of chloroform. The thus obtained mixture was stored as a cDNA library at 4° C.

Step 6 (Cloning of a cDNA clone containing the nucleic acid of NANBV from the cDNA library)

Escherichia coli strain Y1090 provided with the same cDNA cloning kit as used in Step 4 of Example 1 was cultured at 37° C. in 50 ml of an LBM medium containing 1 w/v % trypton, 0.5 w/v % yeast extract, 1 w/v % sodium chloride and 50 µg/ml ampicillin. When the cells of the strain were grown to a logarithmic growth phase and the cell concentration became 2.5×10$^8$/ml, the cells were collected by centrifugation at 3,000 rpm for 5 min and suspended in 4 ml of a 10 mM aqueous magnesium sulfate which had been cooled in ice. The mixture containing the recombinant λgt11 phages obtained in Step 5 of Example 1 was diluted with a SM-buffer containing 0.1M sodium chloride, 8 mM magnesium sulfate, 50 mM Tris-HCl and 0.01% gelatin. 0.1 ml of the obtained diluted phage solution and 0.1 ml of the above-obtained cell suspension were mixed together and the mixture was incubated at 37° C. for 15 min to introduce the recombinant phages into cells of Escherichia coli. Then, to the mixture, 3 ml of a soft agar medium (1 w/v trypton, 0.5 w/v % yeast extract, 0.5 w/v % sodium chloride, 0.25 w/v % magnesium sulfate, 0.7 w/v % agar, pH 7.0) heated at 45° C. was added. The resultant mixture was overlaid on fifty L agar plates (1 w/v % trypton, 0.5 w/v % yeast extract, 1 w/v % sodium chloride, 1.5 w/v % agar, 100 µg/ml ampicillin, pH 7.0). The overlaid agar was solidified at room temperature and incubated at 42° C. for 3 hours. Thereafter, 10 mM IPTG (Isopropyl β-D-thiogalactopyranoside) was infiltrated into the resultant agar plate. The above-mentioned procedure was repeated 60 times to thereby obtain 3,000 agar plates. Then, a dried nitrocellulose filter was bonded to each of the plates and incubated at 37° C. for 3 hours. The resultant filters were separated from the plates and washed three times with a TBS-buffer containing 10 mM Tris-HCl and 150 mM sodium chloride, pH 7.4 and immersed in a 2 w/v % bovine serum albumin solution, followed by incubation at room temperature for 1 hour to block the unreacted portion on the surface of each of the filters.

On the other hand, 1/20 volume of an *Escherichia coli* lysing solution provided with a commercially available immunoscreening kit (manufactured and sold by Amersham International, England) was added to a pooled serum from a convalescent patient having acute NANB hepatitis and the mixture was incubated at room temperature for 30 min. The resultant mixture was diluted with a TBS buffer containing 0.2% of a bovine serum albumin. Thus, a solution containing a primary antibody was obtained (Primary antibody solution A). Substantially the same procedure as mentioned above was repeated except that a serum from a patient having chronic NANB hepatitis was used as a serum, to thereby obtain a solution containing another primary antibody (Primary antibody solution B).

Each of the above-mentioned filters was immersed in Primary antibody solution A at room temperature for 1 hour. Each of the resultant filters was washed four times with a TBST buffer containing 0.05% of Tween 20 (surfactant). Each of the washed filters was immersed in a secondary antibody solution which had been prepared by diluting a peroxidase-labeled human IgG antibody (manufactured and sold by Cappel Co., Ltd., West Germany) 1,000-fold with a TBS buffer containing 0.2 w/w % gelatin. The resultant filter was allowed to stand at room temperature for 1 hour and well washed with a TBST buffer, followed by immersion in a mixture of 50 ml of a TBS buffer, 0.4 ml of DAB (3,3'-diaminobenzidine tetrahydrochloride) and 15 μl of a 30% aqueous hydrogen peroxide at room temperature for 20 min to allow color development. The resultant filters were completely washed with distilled water and the color development reaction was stopped. Substantially the same procedure as mentioned above was repeated except that Primary antibody solution B was used instead of Primary antibody solution A. Then, the color developed dots (positive dots) on the filters correspond to the plaques (positive plaques) of *E. coli* transfected with recombinant viruses containing the NANBV cDNA. Therefore, the plaques corresponding to the color developed dots were selected.

Thus, 22 positive plaques were selected from about 2,000,000 plaques. The transformant clones corresponding to these 22 positive plaques were isolated and subjected to the above-mentioned plaque hybridization procedure. Thus, 5 positive clones were selected and isolated from the 22 positive clones. Each of the thus obtained positive clones was designated N-1, N-2, N-3, N-4 and N-5, respectively. The clone N-1 and clone N-2 have been deposited with the Fermentation Research Institute of the Agency of Industrial Science and Technology, Japan and assigned Accession No. FERM BP-2416 and No. FERM BP-2431, respectively.

Further, the cDNA prepared in Step 3 of Example 1 was inserted into the λgt11 in substantially the same manners as in Step 6 and Step 7 of Example 1, to thereby prepare another cDNA library. Using the cDNA library, the immunoscreening was conducted in the same manner as mentioned above, to thereby obtain positive clones from about 2,500,000 plaques. From the thus obtained positive clones, one clone was selected and designated N-18.

Clone N-18 has been deposited at the Fermentation Research Institute and assigned Accession No. FERM BP-2418.

Then, the reactivity of the expression product of each clone with the serum shown in Table 2 below was examined in the same manner as in Step 4 in Example 1. The results are shown in Table 2. The expression products of these clones were specifically reacted with one or both of a serum from a convalescent patient having acute NANB hepatitis and a serum from a patient having chronic NANB hepatitis. However, all of the expression products of the obtained clones were not reacted with a serum from a healthy human adult and with a serum from a patient having hepatitis B.

TABLE 2

| clone No. | serum from healthy human adult | serum of hepatitis B patient | convalescent serum of acute NANB hepatitis patient | serum of chronic NANB hepatitis patient |
|---|---|---|---|---|
| N-1 | − | − | + | − |
| N-2 | − | − | − | + |
| N-3 | − | − | + | + |
| N-4 | − | − | − | + |
| N-5 | − | − | − | + |
| N-18 | − | − | + | + |

Reactivity: "+" means positive and "−" means negative.

As apparent from Table 2, the expression products of clone N-3 and clone N-18 exhibited an antigen-antibody reaction with both a serum from a convalescent patient having acute NANB hepatitis and a serum from a patient having chronic NANB hepatitis. On the other hand, the expression product of clone N-1 exhibited an antigen-antibody reaction only with a serum from a patient having acute NANB hepatitis, and the expression product of clone N-2, clone N-4 and clone N-5 exhibited an antigen-antibody reaction only with a serum from a patient having chronic NANB hepatitis. This suggests that the expression product of clone N-3 or N-18 can be used for diagnosing acute NANB hepatitis and chronic NANB hepatitis, and that the expression product of clone N-1 can be used for diagnosing acute NANB hepatitis, and the expression product of clone N-2, N-4 or N-5 can be used for diagnosing chronic NANB hepatitis.

Step 7 (Expression of NANBV cDNA clone in a large amount)

The *E. coli* transformant strain N-1 obtained in Step 6 of Example 1 was cultured. From the culture, a phage DNA was isolated and subjected to phenol extraction and ethanol precipitation to obtain a purified phage DNA. The thus purified phage DNA was digested with restriction enzyme EcoRI and subjected to low-melting point agarose gel electrophoresis, and a portion of the agarose gel containing a band of the NANBV cDNA was cut off. To the cut-off agarose gel was added 0.5 ml of a TEN buffer containing 10 mM Tris-HCl, 1 mM EDTA and 10 mM NaCl (pH 7.5), and the mixture was heated at 65° C., followed by phenol extraction and ethanol purification to thereby obtain an NANBV cDNA fragment. The thus obtained NANBV cDNA fragment was inserted in a vector containing a promoter capable of exhibiting a high level of gene expression in cells of *Escherichia coli*. That is, a plasmid pSN518 DNA (Amemura, M., Shinagawa, H., Makino, K., Otsuji, N. & Nakata, A., 1982, J. Bacteriol. Vol. 152, pp. 692–701; and U.S. Pat. No. 4,703,005) containing a gene coding for a phosphate-binding protein (phoS), derived from *Escherichia coli* was digested with restriction enzyme HpaI. From the digests, a DNA fragment of 6.3 kb was isolated by electrophoresis in the same manner as mentioned above. The obtained DNA fragment was dissolved in 100 μl of a Bal31 buffer containing 12 mM calcium chloride, 12 mM magnesium chloride, 0.2M sodium chloride, 20 mM Tris-HCl (pH 8.0) and 1 mM EDTA, and heated at 30° C. for 3 min. To the resultant solution was added 0.5 unit of nuclease Bal31 (manufactured and sold by Takara Shuzo Co., Ltd., Japan) and a reaction was conducted at 30° C. for 6 min. To the reaction mixture, 20 mM EDTA was added to terminate the reaction. The reaction mixture was subjected to phenol extraction and ethanol precipitation to obtain a DNA fragment. Then, an EcoRI linker was added to both ends of the DNA fragment in the same manner as described in Step 5 of Example 1, and the resultant DNA fragment was ligated to the above-obtained NANBV cDNA fragment. With the resultant recombinant plasmid, cells of *Escherichia coli* strain DH1 (Proc. Nat. Acad. Sci., U.S.A., 60, p.160, 1968) were transformed. With respect to the thus obtained transformants, the transformants having a recombinant plasmid containing the NANBV cDNA were detected using a $^{32}$P-dCTP labeled probe prepared from the NANBV cDNA by a nick translation kit (manufactured and sold by Amersham International, England). Thus, 32 transformants were found to have a recombinant plasmid containing the NANBV cDNA. From each of the transformants, the plasmid DNA was isolated by phenol extraction and ethanol precipitation in the manner as mentioned above. The plasmid DNA was partially digested with restriction enzyme EcoRI, followed by phenol extraction and ethanol precipitation. The resultant DNA fragment was dissolved in a buffer containing 70 mM Tris-HCl (pH 7.5), 10 mM magnesium chloride, 5 mM dithiothreitol and 200 μM dNTP (a mixture of dATP, dCTP, dGTP and dTTP). To the solution was added T4 DNA polymerase (manufactured and sold by Takara Shuzo Co., Ltd., Japan) and the mixture was heated at 37° C. for 30 min. The resultant solution was subjected to phenol extraction and ethanol precipitation to obtain a DNA. Using the thus obtained DNA and a universal terminator (manufactured and sold by Pharmacia Fine Chemicals AB, Sweden) having a translation termination codon, a plasmid was prepared in substantially the same manner as described in Step 4 of Example 1. Then, with the thus obtained plasmid, the *Escherichia coli* strain DH1 was transformed to obtain a transformant clone. The above-mentioned procedure was conducted with respect to each of the 32 transformants obtained above. Thus, 32 transformant clones were obtained. The colony of each of the clones was isolated and cultured at 37° C. overnight in a Tris-HCl (pH 7.2) buffer medium containing 0.2 w/v % of glucose and 0.64 mM potassium dihydrogenphosphate, and the cultured cells were collected. The collected cells were suspended in an equivolume of the same buffer medium as mentioned above except that the concentration of potassium primary phosphate was changed to 0.064 mM, and the suspention was incubated at 37° C. for 6 hours while shaking. From the resultant culture, cells were collected and suspended in 50 mM phosphate buffer (pH 7.2) containing 0.15M NaCl, and the suspended cells were disrupted by means of glass beads to obtain a cell homogenate. Then, the amount of an NANBV antigen peptide in the cell homogenate was determined by enzyme-linked immunosorbent assay (ELISA) using the serum from a patient having NANB hepatitis, as follows. A serum from a patient having NANB hepatitis was mixed with Freund's complete adjuvant. With the mixture, a rabbit was hyperimmunized. Then, a hyperimmune serum obtained from the hyperimmunized rabbit was obtained and subjected to ammonium sulfate precipitation, and the precipitate was obtained as an IgG fraction. The obtained fraction was subjected to gel chromatography using Sephacryl S200 (manufactured and sold by Pharmacia Fine Chemicals AB, Sweden) to obtain a purified anti-NANBV IgG. Then, the purified anti-NANBV IgG was dissolved in a 50 mM carbonate buffer (pH 9.6). 100 μl of the solution was put in the wells of a DYNATECH MICROELISA plate (manufactured and sold by Greiner, Co., Ltd., West Germany) and allowed to stand at 4° C. for 18 hours, to thereby immobilize the anti-NANBV IgG on the surface of each well. Each well was washed three times with a phosphate buffer containing 0.05 w/w % Tween 20 (PBS-T). The assay of the NANBV antigen peptide in a cell extract sample was conducted as follows. 5 ml of a sample was diluted with a PBS-T buffer so that the resultant solution became 2-fold volume. The mixture was subjected to centrifugation at 100,000×g at 4° C. for 4 hours to obtain a precipitate. The thus obtained precipitate was dissolved in 0.2 ml of a PBS-T buffer containing 0.1 w/w % of a Triton X-100 and diluted with a PBS-T buffer by doubling dilution to $2^{10}$-fold degree of dilution. 0.1 ml of each of the diluted solutions was added individually to the antibody-immobilized well, followed by reaction at 37° C. for 1 hour. Each well was washed with a PBS-T buffer three times.

On the other hand, the anti-NANBV IgG obtained in the same manner as mentioned above was labeled with horseraddish peroxydase (HRPO) according to the method described in Wilson, M. B. & Nakane, P.: "Immunofluorescence and related techniques (W. W. Knapp, H. Holubar & G. Wick, ed eds.), p. 215 Elsevier/North-Holland, Amsterdam, 1978, to obtain an HRPO-labeled anti-NANBV IgG solution. The solution was diluted 10-fold with a PBS-T buffer containing 10 v/v % fetal calf serum.

The diluted HRPO-labeled anti-NANBV IgG solution was added to each well, and incubated at 37° C. for 1 hour to advance a reaction. The wells were washed with PBS-T three times. 0.1 ml of a 0.05M citrate-phosphate buffer (pH 5.0) containing 0.5 mg/ml of o-phenylenediamine as a coloring agent and 2 μl/ml of peroxide as a substrate was added to each well, and incubated for 40 min out of the light. 0.1 ml of 4N sulfate was added to each well to terminate the reaction. The ELISA titer of the reaction mixture in each well was determined by measuring the optical density at 490 nm ($OD_{490}$). Based on the amount of an NANBV antigen peptide in terms of an ELISA titer, five clones OA-18, OA-101, OA-118, OA-190 and OA-270 which exhibited high ELISA titer were obtained. Of these, clone OA-101 and OA-118 exhibiting higher ELISA titer were selected. The results are shown in Table 3(a).

Substantially the same procedure as mentioned above was conducted except that clone N-18 was used instead of clone N-1. Thus, five clones OC-11, OC-25, OC-27, OE-8 and OB-13 which exhibited high ELISA titer were obtained. Of these, clone OE-8 exhibiting higher ELISA titer was selected. The results are shown in Table 3(b).

The results show that the selected clones OA-101, OA-118 and OE-8 produced an NANBV antigen peptide in a large amount.

TABLE 3(a)

| Clone | Degree of dilution of cell extract | ELISA titer OD$_{490}$ |
| --- | --- | --- |
| OA-18 | 1:80 | 0.074 |
| OA-101 | 1:80 | 1.416 |
| OA-118 | 1:80 | 0.770 |
| OA-190 | 1:80 | 0.125 |
| OB-270 | 1:80 | 0.068 |
| Escherichia coli (normal) | 1:80 | 0.009 |

TABLE 3(b)

| Clone | Degree of dilution of cell extract | ELISA titer OD$_{490}$ |
| --- | --- | --- |
| OC-11 | 1:80 | 0.080 |
| OC-25 | 1:80 | 0.014 |
| OC-27 | 1:80 | 1.397 |
| OE-8 | 1:80 | 1.890 |
| OB-13 | 1:80 | 0.096 |

Step 8 (Purification of the NANBV antigen)

The *Escherichia coli* clone OA-101 prepared in Step 7 of Example 1 was cultured, and the cell extract containing the NANBV antigen peptide was obtained from the culture. The cell extract was subjected to sucrose density gradient centrifugation at 30,000 rpm for 18 hours using a sucrose gradient of 10 to 50 w/w % and a centrifuge (Model RPZ-35T, zonal rotor, manufactured and sold by Hitachi Koki Co., Ltd., Japan) to obtain an NANBV antigen peptide fraction. This fraction was dialyzed against a 50 mM phosphate buffer (pH 7.2) containing 0.15M NaCl for 24 hours to remove the sucrose. The resultant dialysate was dialyzed against 1/200M phosphate buffer (pH 7.2). Then, to the dialysate was added 40 ml of a 1/200M phosphate buffer containing 40 w/w % of potassium bromide, followed by equilibrium density gradient centrifugation at 45,000 rpm for 48 hours using a centrifuge (manufactured and sold by Hitachi Koki Co., Ltd., Japan, rotor No. RP-50T-2) to obtain an NANBV antigen peptide fraction. The obtained fraction was dialyzed against a 5 mM phosphate buffer (pH 7.2) for 24 hours to remove the potassium bromide. The dialysate was subjected to potassium bromide equilibrium density gradient centrifugation and dialysis in the same manner as mentioned above. Thus, a dialysate containing an NANBV antigen peptide was obtained. Then, 2 ml of the dialysate was subjected to gel filtration chromatography using Sephacryl S200 (manufactured and sold by Pharmacia Fine Chemicals AB, Sweden) column equilibrated with physiological saline. A fraction containing NANBV antigen peptide was pooled. Thus, there was obtained a solution containing a purified NANBV antigen peptide derived from clone OA-101 (Lot A-001a).

Substantially the same procedure as mentioned above was conducted except that clone OE-8 was used instead of clone OA-101, to thereby obtain a solution containing a purified NANBV antigen peptide derived from clone OE-8 (Lot E-001a).

Step 9 (Reactivity of the NANBV antigen peptide produced by clone N-18 with a panel serum)

The reactivity of the antigen peptide produced by clone N-18 with a panel serum was determined according to the immoscreening method described in Step 6 of Example 1 using panel serum A and panel serum B. Panel serum A comprised eight sera from convalescent patients having NANB hepatitis, thirteen sera from patients having chronic NANB hepatitis, five sera from patients having chronic hepatitis B and five sera from healthy humans diagnosed as negative to hepatitis. Panel serum B comprised five sera from patients having chronic NANB hepatitis, one serum from a patient having acute NANB hepatitis, two sera from patients having alcoholic chronic hepatitis and five sera from healthy humans diagnosed as negative to hepatitis. The results are shown in Table 4 and Table 5. In Tables 4 and 5, the positive ratio (ratio of the number of the sera reacted with the NANBV antigen peptide produced by clone N-18 to the number of the sera examined) with respect to each serum group is shown.

The results show that the NANBV antigen peptide did not react with sera from healthy humans and with sera from patients having chronic hepatitis B, but specifically reacted with sera from patients having chronic NANB hepatitis with high reactivity. That is, the positive ratio was 12/13 to 5/5 (92.3% to 100%) as shown in Table 4 and Table 5.

However, the reactivity of the NANBV antigen peptide with sera from convalescent patients having NANB hepatitis was relatively low, that is, the positive ratio was 4/8 (50%) as shown in Table 4. Further, the NANB antigen peptide did not react with a serum from a patient having acute NANB hepatitis as shown in Table 5. These results suggest that in the serum from a convalescent patient from chronic NANB hepatitis and the serum from a patient having acute NANB hepatitis, the antibody against the NANBV antigen had not yet been produced in an amount sufficient to be detected by the NANBV antigen peptide.

TABLE 4

| Panel serum A | Positive ratio | (%) |
| --- | --- | --- |
| Sera from convalescent patients having NANB hepatitis | 4/8 | (50) |
| Sera from patients having chronic NANB hepatitis | 12/13 | (92.3) |
| Sera from patients having chronic hepatitis B | 0/5 | (0) |
| Sera from healthy humans | 0/5 | (0) |

TABLE 5

| Panel serum B | Positive ratio | (%) |
| --- | --- | --- |
| Sera from patients having chronic NANB hepatitis | 5/5 | (100) |
| Serum from a patient having acute NANB hepatitis | 0/1 | (0) |
| Sera from patients having alcoholic chronic hepatitis | 0/2 | (0) |
| Sera from a healthy humans | 0/5 | (0) |

Step 10 (Determination of the nucleotide sequences of the NANBV cDNA's contained in clone N-1, clone N-2 and clone N-18)

Escherichia coli strain N-1 obtained in Step 6 of Example 1 was cultured and the recombinant phage DNA was isolated from the cultured cells of the strain N-1 in the same manner as in Step 7 of Example 1. The recombinant phage DNA was digested with restriction enzyme EcoRI, and an NANBV cDNA fragment was isolated in the same manner as described in Step 7 of Example 1. The obtained fragment was inserted in the vector plasmid pUC19 (manufactured and sold by Takara Shuzo Co., Ltd., Japan) compatible with Escherichia coli. That is, 1 μg of vector plasmid pUC19 was dissolved in 30 μl of a buffer solution containing 100 mM Tris-HCl (pH 7.5), 7 mM $MgCl_2$ and 100 mM NaCl. To the resultant solution was added 1 μl of EcoRI (manufactured and sold by Takara Shuzo Co., Ltd., Japan). The mixture was incubated at 37° C. for 60 min. Then, to the resultant reaction mixture were added 10 μl of an alkaline phosphatase buffer containing 100 mM Tris-HCl (pH 8.0), 1M KCl and 10 mM $MgSO_4$, 59 μl of distilled water and 1 μl of alkaline phosphatase (manufactured and sold by Takara Shuzo Co., Ltd., Japan), and the mixture was incubated at 60° C. for 2 hours to advance a reaction. The reaction mixture was subjected to phenol extraction twice and the obtained aqueous layers were pooled. To the aqueous layer were added 1/10 volume of 3M acetate buffer (pH 4.8) and 2-fold volume of ethanol and the resultant mixture was cooled to −20° C. to precipitate a DNA, followed by centrifugation at 12,000 rpm for 5 min to separate the DNA precipitate. The precipitate was dried to obtain a vector plasmid DNA. The phosphate residue at the 5'-end portion of the vector plasmid DNA had been removed by the above-mentioned treatment with alkaline phosphatase. Then, 0.1 μg of the vector plasmid DNA and 0.1 μg of the above-obtained NANBV cDNA fragment were dissolved in a buffer solution containing 66 mM Tris-HCl (pH 7.6), 66 mM $MgCl_2$, 10 mM dithiothreitol and 0.1 mM adenosine 5'-triphosphate. To the resultant solution was added 1 μl of a ligase (manufactured and sold by Takara Shuzo Co., Ltd., Japan). The mixture was incubated at 16° C. for 3 hours, followed by phenol extraction and ethanol precipitation to collect a DNA. Then, with the collected DNA, Escherichia coli strain JM109 (manufactured and sold by Takara Shuzo Co., Ltd., Japan) was transformed by the calcium-rubidium method mentioned hereinbefore, followed by culturing. Thus, a transformant clone having a recombinant plasmid containing the NANBV cDNA inserted therein was obtained. The recombinant plasmid was isolated from the above-obtained transformant clone and digested with restriction enzyme EcoRI. The resultant digests were subjected to determination of the nucleotide sequence using 7-DEAZA sequencing kit (manufactured and sold by Takara Shuzo Co., Ltd., Japan) according to the method described in Mizusawa, S., Nishimura, S. and Seela, F., Nucleic Acids Res., 14, 1319–1324, (1986).

Substantially the same procedure as mentioned above was conducted except that each of clone N-2 and clone N-18 was individually used instead of clone N-1.

As a result, it was found that the transformant clone N-1 contained the NANBV cDNA having a nucleotide sequence shown in FIG. 2(a); the transformant clone N-2 contained the NANBV cDNA's having nucleotide sequences shown in FIGS. 2(e) and 2(f); and the transformant clone N-18 contained the NANBV cDNA's having nucleotide sequences shown in FIGS. 2(a), 2(b), 2(c) and 2(d).

EXAMPLE 2

Extraction of a messenger RNA derived from a liver tissue for preparing a cDNA 1 g of a liver tissue obtained from a patient having NANB hepatitis by hepatectomy was cut into small pieces. 10 ml of a solution containing 4M guanidine thiocyanate as used in Step 1 of Example 1 was added to the liver tissue pieces and the liver tissue pieces were homogenated. Then, an RNA was extracted from the homogenate and purified in substantially the same manner as in Step 1 of Example 1, to obtain a solution containing an RNA. Then, from the solution, an RNA derived from the liver tissue was isolated using the oligo (dT) column (0.5 ml).

The thus obtained RNA obtained can be used instead of the RNA obtained in Step 1 of Example 1, for producing an NANBV cDNA according to substantially the same method as described in Steps 2 to 8 of Example 1.

EXAMPLE 3

Step 1 (Preparation of a diagnostic agent for use in the enzyme-labeled immunosorbent assay (ELISA))

Using the NANBV antigen peptide Lot A-001a prepared in Step 8 of Example 1, an anti-NANBV antigen peptide IgG was prepared (Lot A-1) and labeled with HRPO in substantially the same manner as described in Step 7 of Example 1, to thereby obtain an HRPO-labeled anti-NANBV antigen peptide IgG A-1 as a diagnostic agent.

Substantially the same procedure as mentioned above was conducted except that the NANBV antigen peptide Lot E-001a was used instead of the NANBV antigen peptide Lot A-001a, to prepare another anti-NANBV antigen peptide IgG (Lot E-3) and label the IgG with HRPO. Thus, an HRPO-labeled anti-NANBV antigen peptide IgG E-3 was obtained as a diagnostic agent.

Using the above-obtained HRPO-labeled IgG's A-1 and E-3, the amount of the NANBV antigen in each of serum samples A, B and C from patients having NANB hepatitis and a serum from a healthy human was determined by ELISA in the same manner as in Step 7 of Example 1. The results are shown in Table 6.

TABLE 6

| Serum sample | NANB antigen in serum (ELISA titer, $OD_{490}$) | |
|---|---|---|
| | fixed antibody: A-1 | E-3 |
| A | 0.171 | 0.250 |
| B | 0.302 | 0.390 |
| C | 0.205 | 0.310 |
| Serum from healthy human | 0.023 | 0.018 |

Step 2 (Preparation of a diagnostic agent for use in a passive hemagglutination (PHA) method or a reverse passive hemagglutination (rPHA) method)

Blood of a sheep was collected and filtered through a cotton cloth. Then, hemocytes remaining on the cotton cloth unfiltered were washed five times with 13 mM phosphate buffer containing 0.15M NaCl (PBS). 0.4 ml of the resultant hemocytes was suspended in 10 ml of PBS. Then, the NANBV antigen peptide was adsorbed and fixed on the hemocytes in the above-obtained suspension according to the method of Avramea et al, Immunochemistry, 6, p.67, 69. That is, to the above-obtained suspension containing the fixed hemocytes was added 1 ml of a solution containing the purified NANBV antigen peptide (Lot A-001a) obtained in Example 1 at a concentration of 25 mg/ml and stirred. Then, 3 ml of a PBS containing 2.5 w/w % of glutaraldehyde was dropwise added to the suspension and stirred at room temperature for 1 hour. Then, the cells in the resultant mixture were collected by centrifugation and washed with the PBS five times. The washed cells were suspended in 1 ml of a 1.0M glycine buffer (pH 7.2) and the suspension was allowed to stand for 1 hour. From the resultant suspension, cells were collected by centrifugation and washed with the PBS five times. The cells were suspended in a PBS containing 1 v/v % of a normal sheep serum at a cell concentration of 1 w/w %. Using the suspension, the reactivity of the NANBV antigen peptide with serum samples D to H from NANB hepatitis patients and with a serum from a healthy human adult diagnosed as negative to hepatitis was determined by the PHA method. Substantially the same procedure as mentioned above was conducted except that a solution containing the NANBV antigen peptide (Lot E-001a) was used. The results are shown in Table 7.

Substantially the same procedure as mentioned above was conducted except that each of the anti-NANBV antigen peptide IgG's Lot A-1 and Lot E-3 obtained in Step 1 of Example 3 was individually used instead of the NANBV antigen peptide, to thereby obtain a suspension containing the antibody. Using the suspension, the reactivity of the anti-NANBV antigen peptide IgG with each of serum samples A to C from NANB hepatitis patients and with a serum from a healthy human adult diagnosed as negative to hepatitis was determined by the rPHA method. The results are shown in Table 8.

TABLE 7

| Serum sample | anti-NANBV antibody in serum (PHA value, $2^n$) | |
|---|---|---|
| | fixed antigen: Lot A-001a | Lot E-001a |
| D | n = 6 | n = 7 |
| E | 8 | 8 |
| F | 5 | 5 |
| G | 11 | >11 |
| H | 6 | 8 |
| serum from healthy human | <1 | <1 |

TABLE 8

| Serum sample | NANBV antigen in serum (rPHA value, $2^n$) | |
|---|---|---|
| | fixed antibody: A-1 | E-3 |
| A | 4 | 5 |
| B | 6 | 5 |
| C | 6 | 7 |
| serum from healthy human | <1 | <1 |

Step 3 (Preparation of a diagnostic agent for use in the radioimmunoassay (RIA))

(1) Detection of an antibody against the NANBV in serum

The purified anti-NANBV IgG A-1 prepared in Step 1 of Example 3 was labeled with $^{125}I$ by the chloramine T method (Greenwood et al, Biochemical Journal, 80, p.114, 1963). Illustratively stated, 4 ml of the purified IgG (5 mg/ml) was cooled in ice water, and 1 mCi/10 $\mu$l of $^{125}I$ was added to the IgG while gently stirring. Then, 1 ml of a 200 $\mu$g/ml aqueous chloramine T was dropwise added to the mixture and stirred for 5 min to advance a reaction. 1 ml of a 200 $\mu$g/ml aqueous sodium methabisulfite was added to the resultant mixture to terminate the reaction. The resultant mixture was dialyzed to remove the unreacted $^{125}I$, to thereby obtain $^{125}I$-labeled anti-NANBV antigen peptide IgG A 1.

On the other hand, an NANB antigen peptide-fixed beads was prepared as follows. To the NANB antigen peptide Lot A-001a obtained in Step 8 of Example 1 was added polystylene beads treated with glutaraldehyde. The mixture was allowed to stand overnight at 4° C. to fix the antigen peptide on the surface of the beads. For preventing a non-specific reaction of the antigen peptide-fixed beads with substances other than an antibody against the NANBV, bovine serum alubumin was added to the antigen peptide-fixed beads, and the mixture was allowed to stand at 4° C. overnight. Thus, the NANBV antigen peptide(Lot A-001a)-fixed beads were obtained as a diagnostic agent.

Using the above obtained $^{125}I$-labeled anti-NANBV antigen peptide IgG A-1 and the NANBV antigen peptide(Lot A-001a)-fixed beads, an antibody against the NANB antigen peptide in each of serum samples D to F from patients having NANB hepatitis, a serum from a healthy person and a serum from a rabbit hyperimmunized with the NANBV antigen peptide was detected by RIA. That is, 0.1 ml of the $^{125}I$-labeled labeled antibody was put in each of the wells of a reaction tray for the RIA and, further, 0.1 ml of a serum sample was added to each well. Then, the antigen peptide-fixed beads were added to each well and allowed to stand overnight at room temperature to advance a reaction. The resultant beads were sufficiently washed with distilled water. The radioactivity (cpm) of the beads in each well was measured using an auto-gamma-counter. Then, from the radioactivity, an inhibition (%) of the reaction between the $^{125}I$-labeled anti-NANBV antigen peptide IgG and the NANBV antigen peptide-fixed beads was calculated by the following formula, assuming the inhibitions by a serum from a healthy human and a serum from a rabbit hyperimmunized with the NANBV antigen peptide as being 0% and 100%, respectively:

$$\frac{(a - b) - c}{a - b} \times 100 \ (\%),$$

wherein a is the radioactivity (cpm) obtained with respect to a serum from a healthy human, b is the radioactivity (cpm) obtained with respect to a serum from a rabbit hyperimmunized with the NANBV antigen peptide, and c is the radioactivity (cpm) obtained with respect to a serum sample from an NANB hepatitis patient.

The results are shown in Table 9.

Substantially the same procedure as mentioned above was conducted except that the anti-NANBV antigen peptide IgG Lot E-3 was used instead of the IgG Lot A-1, to obtain another $^{125}$I-labeled anti-NANBV antigen peptide IgG E-3. Further, substantially the same precedure as mentioned above was conducted except that the NANBV antigen peptide Lot E-001a was used instead of the antigen peptide Lot A-001a, to obtain another NANBV antigen peptide(Lot E-001a)-fixed beads as a diagnostic agent. Using the $^{125}$I-labeled anti-NANBV antigen peptide E-3 the antigen peptide(Lot E-001a)-fixed beads, the assay of the serum samples was conducted in the same manner as mentioned above. The results are also shown in Table 9.

When the serum sample contained an antibody against the NANBV as Samples D to F, the reaction between the NANBV antigen peptide-fixed beads and the $^{125}$I-labeled anti-NANBV antigen peptide IgG was inhibited by the reaction between the antigen peptide-fixed beads and the anti-NANBV antibody present in the serum. Therefore, the radioactivity of the beads ascribed to the labeled antibody bonded to the beads was relatively low, and the inhibition between the labeled anti-NANBV antigen peptide and the antigen peptide-fixed beads was as high as 74 to 100%.

TABLE 9

| Serum sample | Fixed antigen | |
|---|---|---|
| | Lot A-001a cpm, inhibition (%) | Lot E-001a cpm, inhibition (%) |
| F | 1433 (89) | 1004 (93) |
| G | 155 (99) | 162 (100) |
| H | 3387 (74) | 3260 (77) |
| Healthy human serum | 13025 (0) | 13630 (0) |
| Hyperimmunized rabbit serum | 145 (100) | 160 (100) |

(2) Detection of an NANBV antigen in serum

An anti-NANBV antigen peptide IgG-fixed beads were prepared in substantially the same manner as mentioned above except that the anti-NANBV antigen peptide IgG Lot A-1 was used instead of the NANBV antigen peptide Lot A-001a.

Using the above-obtained $^{125}$I-labeled anti-NANBV antigen peptide IgG A-1 and the anti-NANBV antigen peptide IgG(Lot A-1)-fixed beads, an NANBV antigen present in each of serum samples A to C from patients having NANB hepatitis and a serum from a healthy human was detected in substantially the same manner as mentioned above. The results are shown in Table 10.

Further, the detection of an NANBV antigen in the serum samples was also conducted using another $^{125}$I-labeled anti-NANBV antigen peptide IgG E-3 obtained above, and another anti-NANBV antigen peptide IgG(Lot E-3)-fixed beads prepared from the anti-NANBV antigen peptide IgG Lot E-3 in the same manner as mentioned above. The results are also shown in Table 10.

TABLE 10

| Serum sample | Fixed antibody | |
|---|---|---|
| | Lot A-1 cpm | Lot E-3 cpm |
| A | 790 | 1253 |
| B | 3507 | 5620 |
| C | 1194 | 2004 |
| Serum from | 188 | 195 |

TABLE 10-continued

| Serum sample | Fixed antibody | |
|---|---|---|
| | Lot A-1 cpm | Lot E-3 cpm |
| healthy human | | |

The results show that the serum samples from patients having NANB hepatitis were specifically detected by the use of the $^{125}$I-labeled anti-NANBV antigen peptide IgG and the anti-NANBV antigen peptide-fixed beads.

EXAMPLE 4

Detection of NANBV RNA by a dot hybridyzation method and a Northern blotting method The recombinant phage was isolated from transformant clone N-1 obtained in Step 6 of Example 1 and digested with restriction enzyme EcoRI to obtain a cDNA fragment containing the NANBV cDNA. On the other hand, plasmid pUC19 (manufactured and sold by Takara Shuzo Co., Ltd., Japan) was cleaved by restriction enzyme EcoRI and treated with alkaline phosphatase. 0.1 μg of the above-obtained cDNA fragment, 0.1 μg of the cleaved vector DNA fragment and 5 μl of a 10×ligase reaction solution containing 1.1 mM ATP, 60 mM Tris-HCl (pH 7.6), 66 mM magnesium chloride and 100 mM dithiothreitol, and 0.2 unit of T4 DNA ligase were mixed together, and the volume of the mixture was adjusted to 50 μl by the addition of distilled water. The resultant mixture was incubated at 4° C. for 16 hours, followed by phenol extraction and ethanol precipitation. The thus obtained precipitate was dissolved in 10 μl of a TE buffer, and with the resultant mixture, cells of *Escherichia coli* strain JM109 (manufactured and sold by Takara Shuzo Co., Ltd., Japan) were transformed according to the calcium-rubidium method mentioned hereinbefore. A transformant clone having the NANBV cDNA was selected and isolated using an agar medium plate containing 50 μg/ml of ampicillin.

A $^{32}$P-labeled cDNA for the hybridyzation was prepared as follows. The plasmid DNA was isolated from the above-obtained transformant clone and digested with EcoRI. From the plasmid DNA, the NANBV cDNA was isolated and purified by electrophoresis using a low-melting point agarose gel in the same manner as described in Step 7 of Example 1. Using [α-$^{32}$P]dCTP (3000 Ci/mmol) and an Amersham nick translation kit (manufactured and sold by Amersham International, England), a $^{32}$P-labeled NANBV cDNA was prepared. In order to examine the reactivity of the $^{32}$P-labeled cDNA with a serum from a patient having NANB hepatitis, a dot hybridyzation was conducted using five serum samples from patients having NANB hepatitis, two serum samples from patients having hepatitis B and one serum sample from a healthy human as test specimens and the labeled NANBV cDNA as a probe according to the method described in Step 4 of Example 1. The results are shown in FIG. 1. In Fie. 1, specimens 1 to 5 are sera from patients having NANB hepatitis, specimens 6 and 7 are sera from patients having hepatitis B and specimen 8 is a serum from a healthy human who is diagnosed as negative to hepatitis. As shown in FIG. 1, the labeled NANBV cDNA was specifically hybridized with the sera from patients having NANB hepatitis, but not hybridized with the sera from patients having hepatitis B and with the serum from a healthy human.

On the other hand, the detection of the NANBV RNA was conducted according to a Northern blotting method as follows. That is, an RNA was prepared from each serum specimen in the same manner as in Step 4 of Example 1 and subjected to 6% formaldehyde-agarose gel electrophoresis. The RNA was isolated from the gel, dissolved in 10×SSC (1.5M NaCl and 0.15M sodium citrate) and blotted on a nitrocellulose membrane using an apparatus for transblotting (manufactured and sold by Bio-Rad Laboratories, U.S.A.). The nitrocellulose membrane was subjected to baking at 80° C. for 2 hours and the resultant membrane was immersed in a prehybridyzation solution (50% formaldehyde, 5×SSC (0.75M NaCl and 0.075M sodium citrate), 5×Denhart, 50 mM phosphate-citrate buffer (pH 6.5), 1% glycine, 100 μg/ml salmon sperm DNA), and incubated at 42° C. for 4 hours. Then, the membrane was taken out of the prehybridyzation solution. The single-stranded DNA obtained by heating the above-obtained $^{32}$P-labeled cDNA probe was added to the membrane, followed by incubation at 42° C. for 22 hours to conduct the hybridization. After completion the hybridyzation, the resultant nitrocellulose membrane was washed three times with 2×SSC (0.3M NaCl and 0.03M sodium citrate) containing 0.1% sodium dodecyl sulfate (SDS) and 0.1% pyrophosphoric acid and further washed three times with 0.1×SSC (0.15M NaCl and 0.015M sodium citrate) containing 0.1% SDS and 0.1% pyrophosphoric acid at 50° C. After drying the resultant membrane, autoradiography was conducted to detect the NANBV RNA. The results were substantially the same as those obtained by the above-mentioned dot hybridization.

APPLICATION EXAMPLE 1

Preparation of a purified NANB hepatitis vaccine

To the solution containing the purified NANBV antigen peptide Lot A-001a, which was obtained in Step 8 of Example 1, was added a 0.02% formalin and allowed to stand at 4° C. for 5 days. Then, the resultant formalin-treated NANBV antigen peptide solution was diluted with physiological saline so that the NANBV antigen peptide concentration became 40 μg/ml. The resultant solution was mixed with a physiological saline containing 0.4 mg/ml of an aluminium hydroxide at a volume ratio of 1:1. The mixture was stirred for 30 min, followed by centrifugation at 3,000 rpm for 20 min to obtain a precipitate. The obtained precipitate was suspended in a 13 mM phosphate buffer (pH 7.2) containing 0.15M NaCl to prepare an aluminum-adsorbed NANB hepatitis vaccine.

Substantially the same procedure as mentioned above was conducted except that the NANBV antigen peptide Lot E-001a was used instead of the antigen peptide Lot A-001a, to thereby obtain an aluminum-adsorbed NANB hepatitis vaccine.

An assay for the immunogenicity of the obtained vaccine was conducted according to the standards for preparing an adsorbed vaccine for recombinant hepatitis B vaccine (derived from yeast) described in "Minimum Requirements for Biological Products" mentioned hereinbefore. That is, 1 ml of the above-mentioned vaccine was subcutaneously inoculated to each of mice of 5 weeks old at their backs. 5 weeks after the inoculation, blood samples were collected from the mice, and subjected to passive hemagglutination test to determine the antibody titer in the blood samples. The results are shown in Table 11.

TABLE 11

| Antigen Lot No. | Dilution of vaccine | Average antibody titer ($2^n$) |
|---|---|---|
| A-001a | 1:2 | n = 9.8 |
| | 1:4 | 8.9 |
| | 1:8 | 5.6 |
| | 1:16 | 4.4 |
| E-001a | 1:2 | >10 |
| | 1:4 | 9.7 |
| | 1:8 | 8.5 |
| | 1:16 | 6.9 |
| Physiological saline | | <1.0 |

APPLICATION EXAMPLE 2

Preparation of a monoclonal antibody specific for the NANBV antigen peptide and detection of the NANBV antigen using the monoclonal antibody 20 μg of the purified NANBV antigen peptide Lot E-001a obtained in Step 8 of Example 1 and 20 μg of the Freund's complete adjuvant were mixed together. The mixture was inoculated intraperitoneally to a BALB/c mouse (8-week old) to immunize the mouse. After 3 weeks and 5 weeks, the second immunization and the third immunization were respectively conducted in the same manner as mentioned above. Three days after the third immunization, the spleen of the mouse was excised. The spleen was cut into four masses and pressed by means of a pincer. Then, the masses were filtered through a stainless steel-made sieve (200 mesh Tyler) to obtain spleen cells. The cells were washed and suspended in an NS-1 medium (an RPMI 1640 medium (manufactured and sold by Gibco Co., U.S.A.) containing 15 v/v % fetal calf serum) at a cell concentration of $6 \times 10^7$ cells/ml. 1 ml of the resultant spleen cell suspension and $2 \times 10^7$ cells of myeloma cell line SP-2/0-Ag 14 (ATCC CRL1581) were mixed together and the mixture was subjected to cell fusion in the presence of polyethylene glycol (PEG 6000) according to the method described in "Monoclonal Antibody" by Tatsuo Iwasaki et al, p. 30 (1982), published by Kodansha Scientific, Japan, to thereby obtain three hybridoma clones capable of producing a monoclonal antibody specific for the NANBV antigen peptide. The obtained clones were designated 2-1B-3, 36-7H-5, 38-1C-14, respectively. Each of the clones were individually cultured to produce monoclonal antibodies specific for the NANBV antigen peptide.

Whether or not the NANBV antigen in the liver of an NANBV hepatitis patient can be specifically detected using each of the monoclonal antibodies was examined as follows. A liver tissue obtained by hepatectomy from each of two patients having NANB hepatitis and one patient having hepatitis B was frozen and a tissue slice specimen was prepared from each frozen liver tissue. The specimen was fixed with acetone and reacted separately with the above-obtained monoclonal antibodies at 37° C. for 1 hour according to the method described in "Introduction of Experimental Virology", edited by Gakuyukai of National Institute of Health, Japan, p. 297 (1975), published by Maruzen K. K., Japan. The resultant specimen was sufficiently washed with PBS (0.005M phosphate buffer (pH 7.0) containing 0.1M NaCl). Further, the specimen was reacted with a fluorochrome FITC-labeled anti-mouse IgG (manufactured and sold by Cappel Co., U.S.A.) at 37° C. for 1 hour. The resultant specimen was sufficiently washed with PBS, and observed through a fluorescent microscope to determine whether or not the specimen emitted fluorescence. The specimen which emitted fluorescence was defined as being positive to the NANBV antigen. The results are shown in Table 12.

TABLE 12

| Specimen | Clone No. which produced a monoclonal antibody used | | |
|---|---|---|---|
| | 2-1B-3 | 36-7H-5 | 38-1C-14 |
| Liver tissue obtained from a patient (No. 1) having NANB hepatitis | + | + | + |
| Liver tissue obtained from a patient (No. 2) having NANB hepatitis | + | + | + |
| Liver tissue obtained from a patient having hepatitis B | − | − | − |

Note:
(+) means positive to fluorescence
(−) means negative to fluorescence

As apparent from Table 10, when the monoclonal antibody specific for the NANBV antigen peptide was used for detecting the NANBV antigen in the liver tissue specimen of a patient, the diagnosis of the NANB hepatitis could be conducted with high reliability.

What is claimed is:

1. A cDNA coding for a substantially pure non-A, non-B hepatitis virus antigen peptide, which comprises at least a part of at least one nucleotide sequence selected from the group consisting of formulae (I) to (VI):

(I)
GAATTCCAAAAAGAGCAAAACAAACCGCCGAAGAAA
AAACTAATAAGAGAAG
AAAAGGCGAAGAGACACAGGAAAAAAAAAACAGAGA
CGAAGGTCAGATAGAA
AAAAAGCAAGGAATTC;

(II)
GAATTCCGAGAACAAGACCAGATAAAAACCAAAGACA
GAACACAACAGAGAA
AGACGAAAAGAAGCACCAATCGCAGGCGAAGCAAAA
ACGAAAAAAAAAAAA
AAAGGAATTC;

(III)
GAATTCCAAGAAAAAAGGGAGAAGCCAGCAATGGA
GAAGCCGAAAACGACA
CACACAAGAAACAAAGGAGGTACAAAGAAAAAGAAA
AAACGGCAACAAATAA
CCCAGGAAAGAACAAAAAGCCAAGAGTGGGCAGAAT
AAAAAACTGGAACCGG
GAGGGAAGGAAGGACGCATATCAGATTAGAAAAAGG
AGGGAATTC;

(IV)
GAATTCCTAAGAAATGGCTAGCCCTAGGAGAGGCAGT
CTTTCCCCAGTCAGT
TAGCCCGCAAATGCCAGAGCATCAAGAATTCAGAAAA
GGAGAAAATATAGTT
AATATCAAAGTGGTCGAAGCCTAAGATAGAGAGGTA
GAGAGTATGAAGAGTA
AGACGAATACAAACCAAAATTCTGGAATGATCATTAA
AAACATTATTGATAG
GTACTTAGAAGGGCAAGAGAGGAAGAAGAAAGTAAT
GAGAAATGCTTATGGA
AGCCAAAGGAGCTTTCCAGG
AGAAGAAAGGGAATTC;

(V)
GAATTCCCAACGCGTCGGCTTGGCCCGCGCCTTGGCC
GCCGACCCGCGCTGA
TGGCCGTGGAATTC;

(VI)
GAATTCCGGGGTATTTGCCTCGATCTGCCTGCTCAGC
GCTTCGGCCCTCGGC
TTGGGCGCCCTGCTGCTGGCTTCCGAGCAGCTATTCA
GCGCCTTGAAAGTGG
TTGGCGCGGCGTACGTGTCCGGGAATTC;

wherein the left and right ends of each nucleotide sequence represent the 5'-terminus and 3'-terminus, respectively; and nucleotide sequences individually obtained by substituting at least one nucleotide of each of said nucleotide sequences of formulae (I) to (VI) in accordance with the degeneracy of the genetic code;
said part of at least one nucleotide sequence coding for a peptide which is reactive to a non-A, non-B hepatitis virus antibody.

2. *Escherichia coli* strain N-1 carrying a cDNA coding for a non-A, non-B hepatitis virus antigen peptide, deposited at Fermentation Research Institute, Japan under the accession number FERM BP-2416.

3. *Escherichia coli* strain N-2 carrying a cDNA coding for a non-A, non-B hepatitis virus antigen peptide, deposited at Fermentation Research Institute, Japan under the accession number FERM BP-2431.

4. *Escherichia coli* strain N-18 carrying a cDNA coding for a non-A, non-B hepatitis virus antigen peptide, deposited at Fermentation Research Institute, Japan under the accession number FERM BP-2418.

* * * * *

UNITED STATES PATENT AND TRADEMARK OFFICE
CERTIFICATE OF CORRECTION

PATENT NO. : 5,275,947
DATED : January 4, 1994
INVENTOR(S) : Terukatsu Arima et al It is certified that error appears in the above-indentified patent and that said Letters Patent is hereby corrected as shown below:

On the title page, after item [30] Foreign Application Priority Data insert ---Sept. 30, 1988 [JP] Japan...63-247175---.

Signed and Sealed this

Fourth Day of October, 1994

Attest:

BRUCE LEHMAN

*Attesting Officer*     *Commissioner of Patents and Trademarks*